United States Patent
Sugiyama et al.

(10) Patent No.: US 10,157,465 B2
(45) Date of Patent: Dec. 18, 2018

(54) MEDICAL INFORMATION PROCESSING SYSTEM, NON-TRANSITORY COMPUTER READABLE STORAGE MEDIUM, AND ULTRASOUND DIAGNOSIS APPARATUS

(71) Applicant: Toshiba Medical Systems Corporation, Otawara-shi (JP)

(72) Inventors: Atsuko Sugiyama, Nasushiobara (JP); Yoshimasa Kobayashi, Nasushiobara (JP); Yoshinori Nakatani, Nasushiobara (JP); Katsuhiko Fujimoto, Saitama (JP); Mariko Shibata, Nasushiobara (JP); Natsuki Sato, Kashiwa (JP); Toshie Maruyama, Yaita (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 68 days.

(21) Appl. No.: 14/979,645

(22) Filed: Dec. 28, 2015

(65) Prior Publication Data

US 2016/0110875 A1    Apr. 21, 2016

Related U.S. Application Data

(63) Continuation of application No. PCT/JP2014/067720, filed on Jul. 2, 2014.

(30) Foreign Application Priority Data

Jul. 3, 2013 (JP) .................................. 2013-139974

(51) Int. Cl.
*G06T 7/00* (2017.01)
*A61B 8/08* (2006.01)
*A61B 8/00* (2006.01)

(52) U.S. Cl.
CPC .......... *G06T 7/0081* (2013.01); *A61B 8/0825* (2013.01); *A61B 8/463* (2013.01);
(Continued)

(58) Field of Classification Search
CPC combination set(s) only.
See application file for complete search history.

(56) References Cited

U.S. PATENT DOCUMENTS 6,059,727 A * 5/2000 Fowlkes .................. A61B 8/08
    128/916
6,068,597 A * 5/2000 Lin ...................... A61B 8/0833
    600/443

(Continued)

FOREIGN PATENT DOCUMENTS

| JP | 2008-86742 | 4/2008 |
|----|------------|--------|
| JP | 2008-279272 | 11/2008 |

(Continued)

OTHER PUBLICATIONS

International Search Report dated Sep. 30, 2014 in PCT/2014/067720 filed Jul. 2, 2014 (with English translation).

(Continued)

*Primary Examiner* — Tsung-Yin Tsai
(74) *Attorney, Agent, or Firm* — Oblon, McClelland, Maier & Neustadt, L.L.P.

(57) ABSTRACT

A medical information processing system according to an embodiment includes a storage, and processing circuitry. The storage stores therein a mammography image of a breast of a patient and information indicating an image taking direction of the mammography image. The processing circuitry sets a region of interest in the mammography image. The processing circuitry specifies position information of the region of interest in a schematic drawing that schematically expresses the breast, on the basis of position informa- (Continued)

tion of the region of interest in the mammography image and the information indicating the image taking direction. The processing circuitry outputs the position information of the region of interest in the schematic drawing.

20 Claims, 27 Drawing Sheets

(52) U.S. Cl.
CPC .............. *A61B 8/464* (2013.01); *A61B 8/465* (2013.01); *A61B 8/466* (2013.01); *A61B 8/469* (2013.01); *A61B 8/5292* (2013.01); *G06T 7/0012* (2013.01); *G06T 2207/10016* (2013.01); *G06T 2207/10132* (2013.01); *G06T 2207/30068* (2013.01)

(56) References Cited

U.S. PATENT DOCUMENTS

| | | | | |
|---|---|---|---|---|
| 6,075,879 | A * | 6/2000 | Roehrig | G06F 19/321 382/132 |
| 6,247,812 | B1 * | 6/2001 | Miehle | A61B 3/10 351/206 |
| 6,269,565 | B1 * | 8/2001 | Inbar | G02B 27/024 345/87 |
| 6,421,454 | B1 * | 7/2002 | Burke | A61B 8/4416 382/131 |
| 6,864,826 | B1 * | 3/2005 | Stove | G01N 22/00 342/134 |
| 8,345,979 | B2 * | 1/2013 | Davis | G06T 7/0079 382/181 |
| 2003/0007598 | A1 * | 1/2003 | Wang | A61B 6/463 378/37 |
| 2003/0125621 | A1 * | 7/2003 | Drukker | G06T 7/0012 600/437 |
| 2004/0034304 | A1 * | 2/2004 | Sumi | A61B 8/08 600/439 |
| 2005/0089205 | A1 * | 4/2005 | Kapur | A61B 6/4233 382/128 |
| 2006/0029268 | A1 * | 2/2006 | Endo | A61B 6/463 382/132 |
| 2006/0173319 | A1 * | 8/2006 | Sumi | A61B 8/08 600/437 |
| 2007/0010743 | A1 | 1/2007 | Arai | |
| 2007/0088215 | A1 * | 4/2007 | Thomas Dubberstein | G01S 7/52085 600/437 |
| 2007/0239004 | A1 | 10/2007 | Kakee et al. | |
| 2008/0177180 | A1 * | 7/2008 | Azhari | A61B 8/0825 600/439 |
| 2009/0016580 | A1 * | 1/2009 | Yamamichi | A61B 6/502 382/128 |
| 2009/0097722 | A1 * | 4/2009 | Dekel | G06T 15/10 382/128 |
| 2009/0154782 | A1 * | 6/2009 | Zhang | G06T 3/0081 382/128 |
| 2010/0080439 | A1 * | 4/2010 | Karam | G06K 9/00134 382/133 |
| 2010/0284591 | A1 * | 11/2010 | Arnon | A61B 5/015 382/128 |
| 2011/0123079 | A1 * | 5/2011 | Gustafson | G06F 19/321 382/131 |
| 2011/0142316 | A1 * | 6/2011 | Wang | G06T 11/006 382/131 |
| 2012/0239318 | A1 * | 9/2012 | Tokita | A61B 5/0091 702/56 |
| 2012/0262460 | A1 | 10/2012 | Endo et al. | |
| 2013/0009860 | A1 | 1/2013 | Kameda | |
| 2014/0078866 | A1 * | 3/2014 | Kanamori | A61B 8/4483 367/87 |
| 2014/0121524 | A1 * | 5/2014 | Chiang | A61B 8/463 600/459 |

FOREIGN PATENT DOCUMENTS

| | | |
|---|---|---|
| JP | 2012-217770 | 11/2012 |
| JP | 2013-8274 | 1/2013 |
| JP | 2013-20340 | 1/2013 |

OTHER PUBLICATIONS

Written Opinion dated Sep. 30, 2014 in PCT/2014/067720 filed Jul. 2, 2014.

Yoshiko Seo et al., "Usage experiment of the latest mammography system Usage of scanning information input function (Exam-Marker)", Innervision, vol. 27, (1), 6 pgs. (with partial English translation).

"J-START Comparison test for verifying the efficiency of breast cancer screening using ultrasonography", http://www.j-start.org/, 2013, 3 pgs. (with partial English translation).

Timothy Carter, et al., "MR Navigated Breast Surgery: Method and Initial Clinical Experience", MICCAI, Part II, Lecture Notes in Computer Science, vol. 5242, 2008, 9 pgs.

* cited by examiner

MEDICAL INFORMATION PROCESSING SYSTEM, NON-TRANSITORY COMPUTER READABLE STORAGE MEDIUM, AND ULTRASOUND DIAGNOSIS APPARATUS

CROSS-REFERENCE TO RELATED APPLICATIONS

This application is a continuation of PCT international application Ser. No. PCT/JP2014/067720 filed on Jul. 2, 2014 which designates the United States, incorporated herein by reference, and which claims the benefit of priority from Japanese Patent Application No. 2013-139974, filed on Jul. 3, 2013, the entire contents of which are incorporated herein by reference.

FIELD

Embodiments described herein relate generally to a medical information processing system, a non-transitory computer readable storage medium, and an ultrasound diagnosis apparatus.

BACKGROUND

Conventionally, it has been common that mammary gland image diagnosis processes for breast cancer examinations or the like are performed by using mammography images taken by mammography apparatuses. In contrast, in recent years, a project called "Japan Strategic Anti-cancer Randomized Trial (J-START)" was started, so as to start performing a mammary gland image diagnosis process by using both mammography images and ultrasound images together for breast cancer examinations.

DETAILED DESCRIPTION

A medical information processing system according to an embodiment includes a storage, and processing circuitry. The storage stores therein a mammography image of a breast of a patient and information indicating an image taking direction of the mammography image. The processing circuitry sets a region of interest in the mammography image. The processing circuitry specifies position information of the region of interest in a schematic drawing that schematically expresses the breast, on the basis of position information of the region of interest in the mammography image and the information indicating the image taking direction. The processing circuitry outputs the position information of the region of interest in the schematic drawing.

Exemplary embodiments of a medical information processing system, a medical information processing computer program (hereinafter, "medical information processing program"), and an ultrasound diagnosis apparatus will be explained below, with reference to the accompanying drawings.

First Embodiment

Figure 1:
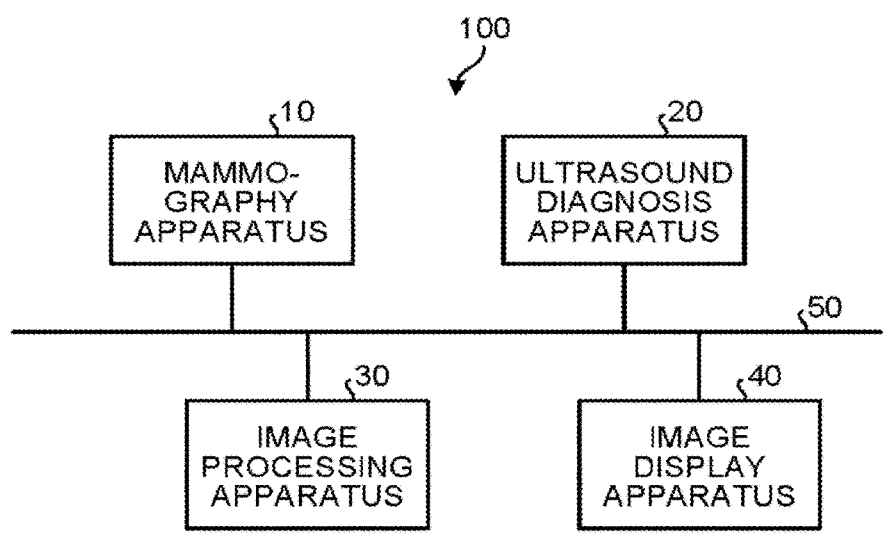
FIG. 1 is a diagram of an exemplary configuration of a medical information processing system according to a first embodiment.

FIG. 1 is a diagram of an exemplary configuration of a medical information processing system according to a first embodiment. The medical information processing system according to the first embodiment is installed in a hospital where a breast cancer examination is carried out and is used for a mammary gland diagnosis process in which both mammography images and ultrasound images are used together. For example, as illustrated in FIG. 1, a medical information processing system 100 according to the first embodiment includes a mammography apparatus 10, an ultrasound diagnosis apparatus 20, an image processing apparatus 30, and an image display apparatus 40. These apparatuses are connected to one another via a network 50 so as to transmit and receive images taken by the mammography apparatus 10 and the ultrasound diagnosis apparatus 20 and the like, to and from one another.

The mammography apparatus 10 is configured to radiate X-rays onto a breast of an examined subject (hereinafter, "patient") to detect X-rays that have passed through the breast, and to generate a mammography image.

Figure 2:
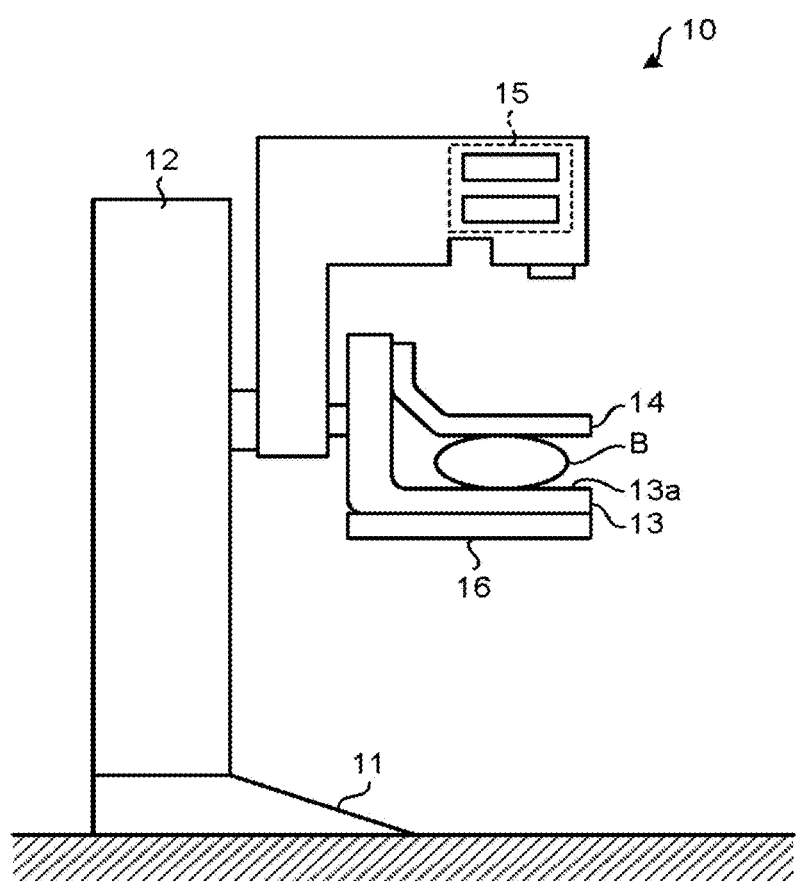
FIG. 2 is a first diagram of an exemplary configuration of a mammography apparatus according to the first embodiment.
Figure 3:
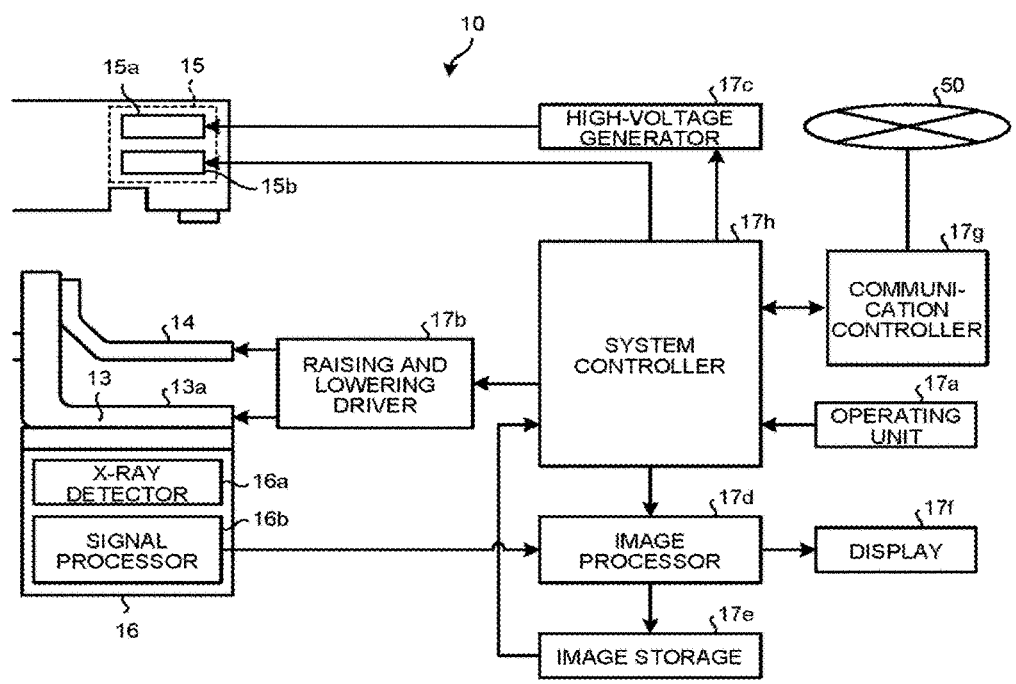
FIG. 3 is a second diagram of the exemplary configuration of the mammography apparatus according to the first embodiment.

FIGS. 2 and 3 are diagrams of an exemplary configuration of the mammography apparatus 10 according to the first embodiment. For example, as illustrated in FIG. 2, the mammography apparatus 10 includes a pedestal 11 and a stand 12. The stand 12 is provided so as to stand on the pedestal 11 and is configured to support an imaging stage 13, a pressing plate 14, an X-ray output unit 15, and an X-ray detecting unit 16. In this situation, the imaging stage 13, the pressing plate 14, and the X-ray detecting unit 16 are supported so as to be movable in up-and-down directions.

The imaging stage 13 is a stage that supports a breast B of the patient and has a supporting surface 13a on which the breast B is placed. The pressing plate 14 is positioned above the imaging stage 13 and is provided so as to be movable in directions to approach and to get away from the imaging stage 13, while opposing the imaging stage 13 in parallel. In this situation, the pressing plate 14 is configured to press the breast B supported by the imaging stage 13, when the pressing plate 14 has moved in the direction to approach the imaging stage 13. The breast B pressed by the pressing plate 14 is flattened and spread so that overlapping of mammary glands in the breast B is reduced.

Further, as illustrated in FIG. 3, the mammography apparatus 10 includes an operating unit 17a, a raising and lowering driver 17b, a high-voltage generator 17c, an image processor 17d, an image storage 17e, a display 17f, a communication controller 17g, and a system controller 17h. The operating unit 17a is configured to receive input operations of various types of commands and the like from an operator. The raising and lowering driver 17b is connected to the imaging stage 13 and is configured to raise and lower the imaging stage 13 in up-and-down directions. Further, the raising and lowering driver 17b is connected to the pressing plate 14 and is configured to raise and lower the pressing plate 14 in up-and-down directions (the directions to approach and to get away from the imaging stage 13).

The X-ray output unit 15 includes an X-ray tube 15a and an X-ray converging device 15b. The X-ray tube 15a is configured to generate the X-rays. The X-ray converging device 15b is positioned between the X-ray tube 15a and the pressing plate 14 and is configured to control the radiation range of the X-rays generated from the X-ray tube 15a. The high-voltage generator 17c is connected to the X-ray tube 15a and is configured to supply a high voltage used by the X-ray tube 15a to generate the X-rays.

The X-ray detecting unit 16 includes an X-ray detector 16a and a signal processor 16b. The X-ray detector 16a is configured to detect X-rays that have passed through the breast B and the imaging stage 13 and convert the detected X-rays into an electrical signal (passed X-ray data). The signal processor 16b is configured to generate X-ray projection data from the electrical signal resulting from the conversion performed by the X-ray detector 16a.

The image processor 17d is connected to the signal processor 16b and the image storage 17e and is configured to generate the mammography image on the basis of the X-ray projection data generated by the signal processor 16b and to store the generated mammography image into the image storage 17e. Further, the image processor 17d is connected to the display 17f and is configured to cause the display 17f to display the generated mammography image. In this situation, the image processor 17d is capable of switching between different types of mammography images to be generated, on the basis of an input operation from the operating unit 17a.

The communication controller 17g is configured to control communication performed with another apparatus via the network 50. For example, the communication controller 17g is configured to transfer the mammography image generated by the image processor 17d to another apparatus via the network 50. The apparatus at the transfer destination is able to perform an image display process or an image processing process on the mammography image transferred thereto via the network 50.

The system controller 17h is connected to the operating unit 17a, the raising and lowering driver 17b, the high-voltage generator 17c, the X-ray converging device 15b, the image processor 17d, and the communication controller 17g and is configured to comprehensively control the entirety of the mammography apparatus 10.

Returning to the description of FIG. 1, the ultrasound diagnosis apparatus 20 is configured to generate an ultrasound image on the basis of reflected-wave data acquired by scanning the patient by using an ultrasound probe that transmits and receives an ultrasound wave.

Figure 4:
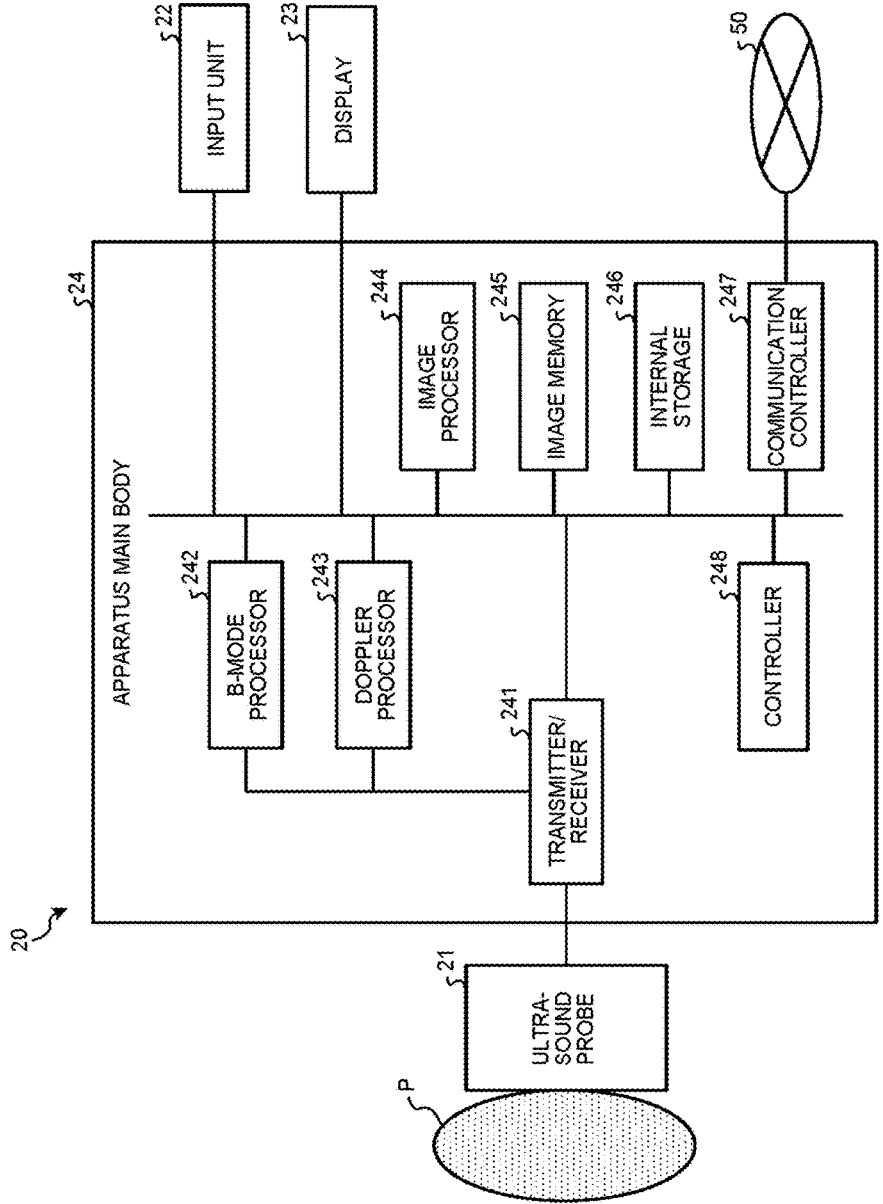
FIG. 4 is a diagram of an exemplary configuration of an ultrasound diagnosis apparatus according to the first embodiment.

FIG. 4 is a diagram of an exemplary configuration of the ultrasound diagnosis apparatus 20 according to the first embodiment. As illustrated in FIG. 4, the ultrasound diagnosis apparatus 20 according to the first embodiment includes an ultrasound probe 21, a display 23, an input unit 22, and an apparatus main body 24.

The ultrasound probe 21 includes a plurality of piezoelectric transducer elements. The plurality of piezoelectric transducer elements are configured to generate an ultrasound pulse on the basis of a drive signal supplied thereto from a transmitter/receiver 241 included in the apparatus main body 24 (explained later), to receive a reflected wave from a patient P, and to convert the received reflected wave into an electric signal. Further, the ultrasound probe 21 includes matching layers provided for the piezoelectric transducer elements, as well as a backing member that prevents ultrasound waves from propagating rearward from the piezoelectric transducer elements.

When the ultrasound pulse is transmitted from the ultrasound probe 21 to the patient P, the transmitted ultrasound pulse is repeatedly reflected on a surface of discontinuity of acoustic impedances at a tissue in the body of the patient P and is received as an echo signal by the plurality of piezoelectric transducer elements included in the ultrasound probe 21. The amplitude of the received echo signal is dependent on the difference between the acoustic impedances on the surface of discontinuity on which the ultrasound pulse is reflected. When the transmitted ultrasound pulse is reflected on the surface of a moving blood flow, a cardiac wall, or the like, the echo signal is, due to the Doppler effect, subject to a frequency shift, depending on a velocity component of the moving members with respect to the ultrasound wave transmission direction.

The display 23 may be a monitor or the like and is configured to display a Graphical User Interface (GUI) used by the operator of the ultrasound diagnosis apparatus 20 to input various types of instructions and setting requests through the input unit 22 and to display an ultrasound image and an analysis result generated by the apparatus main body 24.

The input unit 22 is configured by using a mouse, a keyboard, a button, a panel switch, a touch command screen, a foot switch, and/or a trackball and is connected to the apparatus main body 24. Further, the input unit 22 is configured to receive the various types of instructions and setting requests from the operator of the ultrasound diagnosis apparatus 20 and to transfer the received various types of instructions and setting requests to the apparatus main body 24.

The apparatus main body 24 is configured to generate the ultrasound image on the basis of the reflected waves received by the ultrasound probe 21. As illustrated in FIG. 4, the apparatus main body 24 includes the transmitter/receiver 241, a B-mode processor 242, a Doppler processor 243, an image processor 244, an image memory 245, an internal storage 246, a communication controller 247, and a controller 248.

The transmitter/receiver 241 includes a trigger generating circuit, a transmission delaying circuit, a pulser circuit, and the like and is configured to supply the drive signal to the ultrasound probe 21. The pulse circuit is configured to repeatedly generate a rate pulse for forming an ultrasound pulse having a predetermined Pulse Repetition Frequency (PRF). The PRF may be referred to as a rate frequency. Further, the transmission delaying circuit applies a transmission delay period that is required to converge the ultrasound pulse generated by the ultrasound probe 21 into the form of a beam and to determine transmission directionality and that corresponds to each of the piezoelectric transducer elements, to each of the rate pulses generated by the pulser circuit. Further, the trigger generating circuit applies the drive signal (a drive pulse) to the ultrasound probe 21 with timing based on the rate pulses. In other words, the transmission delaying circuit arbitrarily adjusts the transmission directions from the piezoelectric transducer element surfaces, by varying the transmission delay periods applied to the rate pulses.

Further, the transmitter/receiver 241 has a function to be able to instantly change the transmission frequency, the transmission drive voltage, and the like, for the purpose of executing a predetermined scanning sequence on the basis of an instruction from the controller 248 (explained later). In particular, the configuration to change the transmission drive voltage is realized by using a linear-amplifier-type transmitting circuit of which the value can be instantly switched or by using a mechanism configured to electrically switch between a plurality of power source units.

Further, the transmitter/receiver 241 includes an amplifying circuit, an Analog/Digital (A/D) converter, a reception delaying circuit, an adder, a quadrature detection circuit, and the like and is configured to generate reflected-wave data by performing various types of processes on the reflected-wave signal received by the ultrasound probe 21. The amplifying circuit performs a gain correction process by amplifying the reflected-wave signal for each of channels. The A/D converter applies an A/D conversion to the gain-corrected reflected-wave signals. The reception delaying circuit applies a reception delay period required to determine reception directionality to the digital data. The adder performs an adding process on the reflected-wave signals to which the reception delay period has been applied by the reception delaying circuit. As a result of the adding process performed by the adder, reflected components from the direction corresponding to the reception directionality of the reflected-wave signals are emphasized.

The B-mode processor 242 is configured to receive the reflected-wave data from the transmitter/receiver 241 and to generate data (B-mode data) in which the strength of each signal is expressed by a degree of brightness, by performing a logarithmic amplification, an envelope detection process, and the like on the received reflected-wave data. Further, the B-mode processor 242 is configured to generate M-mode data (explained later).

The Doppler processor 243 is configured to obtain velocity information from the reflected-wave data received from the transmitter/receiver 241 by performing a frequency analysis, to extract bloodstream, tissues, and contrast-agent echo components under the influence of the Doppler effect, and to further generate data (Doppler data) obtained by extracting moving member information such as an average velocity, a dispersion, a power, and the like, for a plurality of points.

The image processor 244 is configured to generate an ultrasound image from the B-mode data and the M-mode data generated by the B-mode processor 242 and the Doppler data generated by the Doppler processor 243. More specifically, the image processor 244 generates a B-mode image from the B-mode data, generates an M-mode image from the M-mode data, and generates a Doppler image from the Doppler data. Further, by performing a coordinate transformation process, a data interpolation process, or the like, the image processor 244 converts (by performing a scan convert process) a scanning line signal sequence from an ultrasound scan into a scanning line signal sequence in a video format used by, for example, television and generates the ultrasound image serving as a displayed image (the B-mode image, the M-mode image, or the Doppler image).

The image memory 245 is a memory configured to store therein the ultrasound image generated by the image processor 244 and an image generated by performing an image processing process on the ultrasound image. For example, after a diagnosis process, the operator is able to invoke any of the images recorded during a medical examination and is able to play back the images as still images or as a moving picture realized with multiple images. Further, the image memory 245 may store therein an image brightness-level signal that has passed through the transmitter/receiver 241, other raw data, image data obtained via the network 50, and the like.

The internal storage 246 is configured to store therein an apparatus control computer program for executing the ultrasound wave transmissions and receptions, image processing processes, and display processes, as well as various types of data such as diagnosis information (e.g., patients' IDs, observations of medical doctors), diagnosis protocols, and/or various types of setting information. Further, the internal storage 246 may also be used for storing any of the images stored in the image memory 245.

The communication controller 247 is configured to control communication performed with another apparatus via the network 50. For example, the communication controller 247 transfers the ultrasound image generated by the image processor 244 to another apparatus via the network 50. The apparatus at the transfer destination is able to perform an image display process or an image processing process on the ultrasound image transferred thereto via the network 50.

The controller 248 is configured to control the entirety of processes performed by the ultrasound diagnosis apparatus 20. The controller 248 includes processing circuitry such as a Central Processing unit (CPU) and a memory and is configured to control operations of the ultrasound diagnosis apparatus 20 by employing the CPU and the memory to execute various types of computer programs. More specifically, on the basis of various types of instructions and setting requests that are input thereto by the operator via the input unit 22 and various types of computer programs and various types of setting information that are read from the internal storage 246, the controller 248 controls processes performed by the transmitter/receiver 241, the B-mode processor 242, the Doppler processor 243, and the image processor 244, and also exercises control so that the display 23 displays the ultrasound image and the like stored in the image memory 245.

Returning to the description of FIG. 1, the image processing apparatus 30 is configured to process the mammography image generated by the mammography apparatus 10, the ultrasound image generated by the ultrasound diagnosis apparatus 20, and the like. The image processing apparatus 30 is primarily used when a mammography examination is performed by a mammography examination technician. Further, the image processing apparatus 30 is configured to receive an input of an observation related to the mammography image from the mammography examination technician and to store therein information indicating the received observation as observation information. For example, the image processing apparatus 30 may be configured by using an image storing server, a workstation, or the like.

The image display apparatus 40 is configured to obtain the mammography image, the ultrasound image, and the observation information related to the mammography image from the image processing apparatus 30 and to display the obtained images and information. The image display apparatus 40 is primarily used when an ultrasound examination is performed by an ultrasound examination technician. For example, the image display apparatus 40 may be a tablet terminal that can be carried around by the operator and that is connectable to the network 50 via a wireless Local Area Network (LAN). Alternatively, the image display apparatus 40 may be a notebook personal computer, for example.

Conventionally, it has been common that mammary gland image diagnosis processes for breast cancer examinations or the like are performed by using mammography images taken by mammography apparatuses. In contrast, in recent years, the project called "Japan Strategic Anti-Cancer Randomized Trial (J-START)" was started so as to start performing a mammary gland image diagnosis process by using both mammography images and ultrasound images together for breast cancer examinations.

Figure 5:
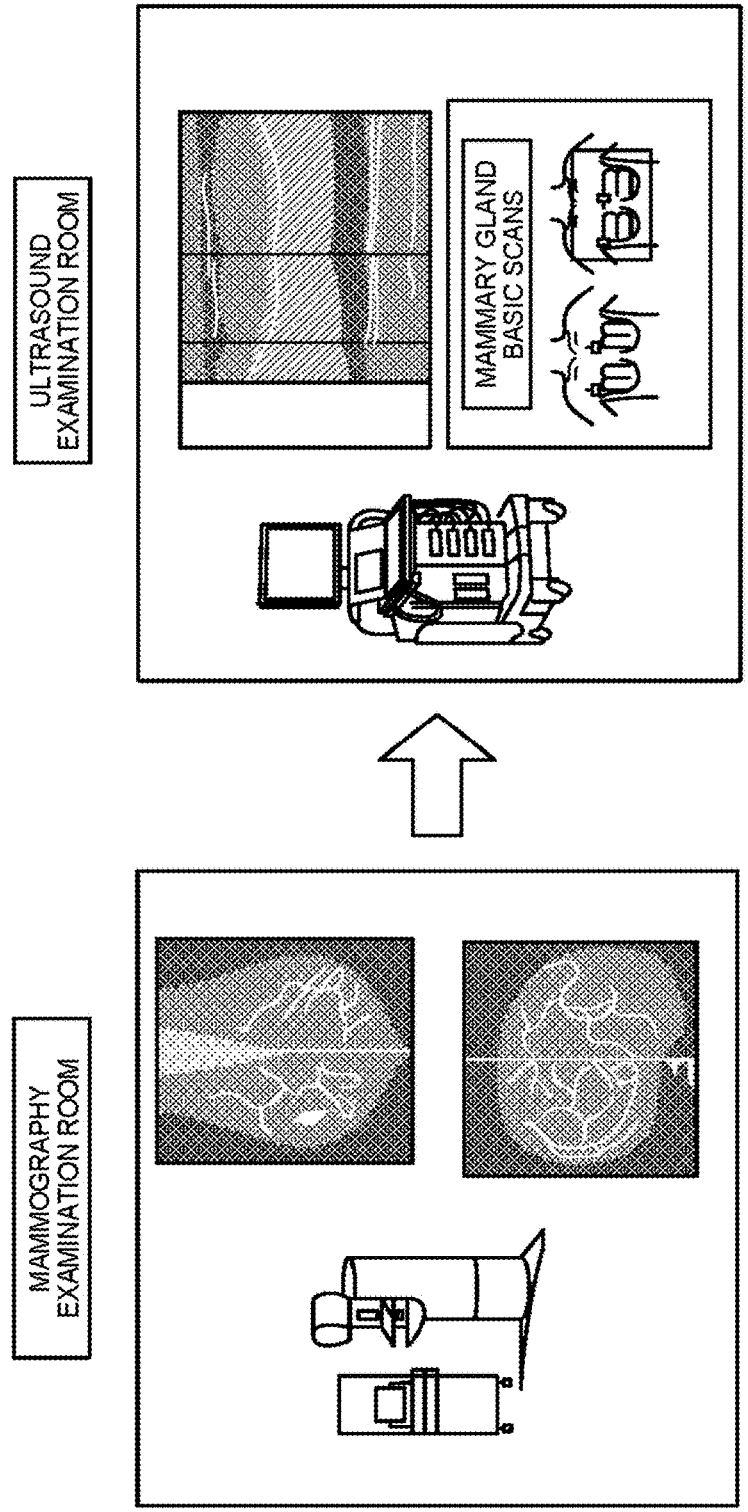
FIG. 5 is a drawing for explaining a mammary gland image diagnosis process in which both mammography images and ultrasound images are used together.

FIG. 5 is a drawing for explaining a mammary gland image diagnosis process in which both mammography images and ultrasound images are used together. For example, as illustrated on the left side of FIG. 5, to perform a mammary gland image diagnosis process by using both mammography images and ultrasound images together, mammography images in a Mediolateral-Oblique (MLO) direction and a Cranio-Caudal (CC) direction are taken, at first, of each of the left and the right breasts of the patient, by using a mammography apparatus. After that, as illustrated on the right side of FIG. 5, an ultrasound image of each of the left and the right of the same patient is taken by using an ultrasound diagnosis apparatus, while referring to the mammography images and observations thereon, on either the same day or a different day.

During such a mammary gland image diagnosis process, generally speaking, in many situations, the technician who takes and interprets the mammography images is a different person from the technician who takes and interprets the ultrasound images. For this reason, conventionally, technicians who are in charge of ultrasound examinations are required to have sufficient knowledge and understanding of interpretations and observations of mammography images, in order to perform the ultrasound examinations while referring to the mammography images and the observations thereon. More specifically, as overall evaluation criteria, the breast cancer examination study committee of the Japan Association of Breast and Thyroid Sonology has already presented the following: "an ultrasound examination should be carefully performed on high-density areas in a mammography image", "When a lump of which the border is clear and smooth is observed in a mammography image, if an ultrasound examination confirms that the lump is evidently a benign lesion (e.g., a simple cyst), no further detailed examination will be required", and "When a focal asymmetric density (FAD) is observed in a mammography image, if an ultrasound examination confirms that the mammary gland is normal, no further detailed examination will be required". Technicians who are in charge of ultrasound examinations are thus required to make these judgements appropriately.

To cope with this situation, according to the first embodiment, the image processing apparatus 30 sets a region of interest in at least one of the mammography images of the breast of the patient and specifies and outputs position information of a region of interest in a schematic drawing that schematically expresses the breast, on the basis of position information of the region of interest in the mammography image and pieces of information indicating image taking directions of the mammography images. As a result, the ultrasound examination technician is able to easily understand the position in the schematic drawing corresponding to the region of interest set in the mammography image. It is therefore possible to improve the level of precision of the mammary gland image diagnosis process. In the following sections, the image processing apparatus 30 according to the first embodiment will be explained in detail.

Figure 6:
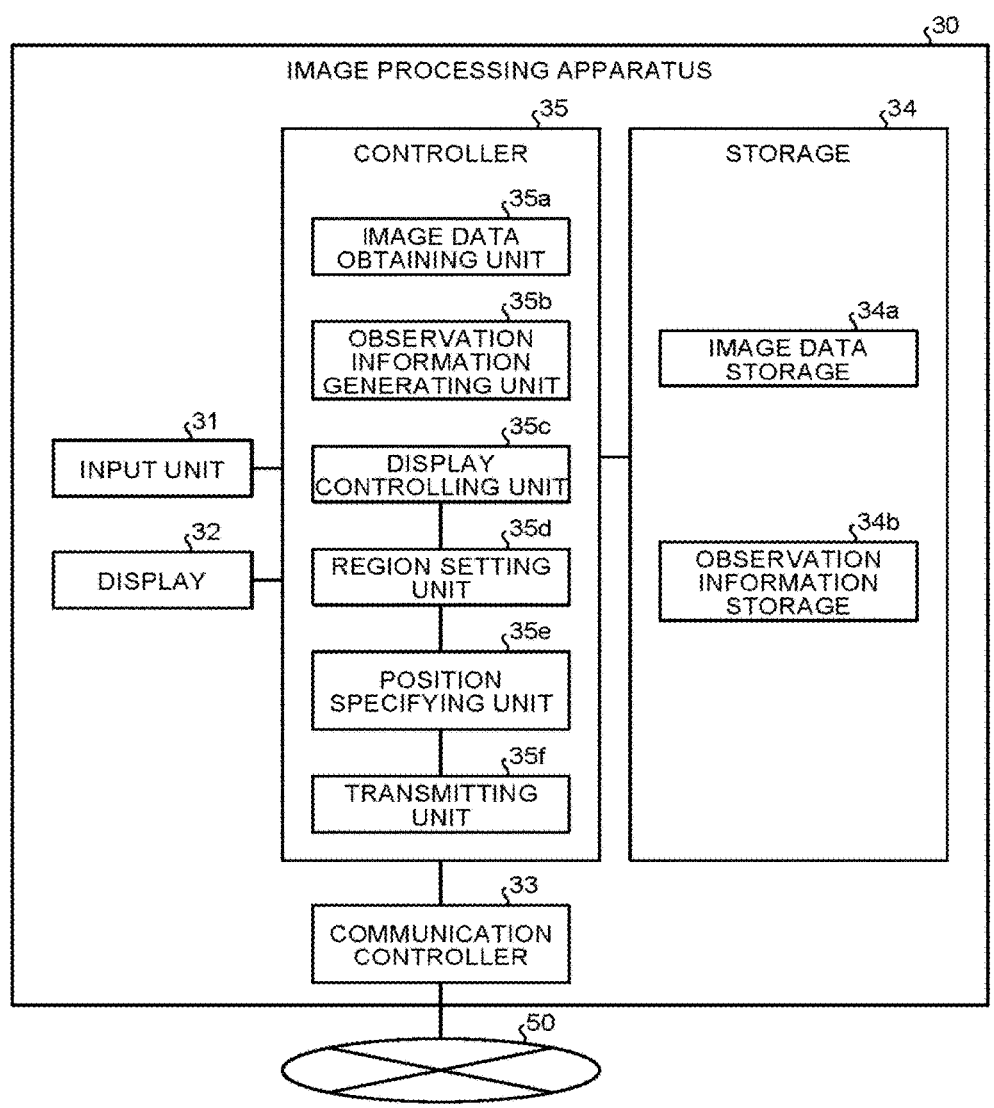
FIG. 6 is a diagram of an exemplary configuration of an image processing apparatus according to the first embodiment.

FIG. 6 is a diagram of an exemplary configuration of the image processing apparatus 30 according to the first embodiment. As illustrated in FIG. 6, the image processing apparatus 30 includes an input unit 31, a display 32, a communication controller 33, a storage 34, and a controller 35.

The input unit 31 is configured to receive inputs of various types of operations and various types of information from an operator. For example, the input unit 31 may be configured by using a keyboard, a mouse, a button, a trackball, and/or a touch panel.

The display 32 is configured to display a GUI used for receiving the various types of operations from the operator and various types of images. For example, the display 32 may be configured by using a liquid crystal display device, a Cathode Ray Tube (CRT) display device, or a touch panel.

The communication controller 33 is configured to control communication performed with another apparatus via the network 50. For example, the communication controller 33 may be configured by using a network card or a network adaptor and may perform the communication with the other apparatus by connecting to the network 50 via an Ethernet (registered trademark) LAN. Alternatively, for example, the communication controller 33 may perform wireless communication with the other apparatus by connecting to the network 50 via a wireless LAN.

The storage 34 is a storage device such as a hard disk, a semiconductor memory, or the like and is configured to store various types of information therein. More specifically, the storage 34 includes an image data storage 34a and an observation information storage 34b.

The image data storage 34a is configured to store therein mammography images obtained by imaging the breast (hereinafter, mammography images of the breast) of the patient and information indicating the image taking directions of the mammography images. More specifically, the image data storage 34a stores therein the mammography images and pieces of information each of which indicates an image taking direction and is kept in association with a corresponding one of the images. An image data obtaining unit 35a (explained later) stores the mammography images and the pieces of information each indicating the image taking direction into the image data storage 34a.

For example, the image data storage 34a stores therein a mammography image in an MLO direction (an MLO image) and a mammography image in a CC direction (a CC image). Further, the pieces of information each indicating the image taking direction in this situation are, for example, pieces of position information each of which is expressed in an apparatus coordinate system of the mammography apparatus. When the mammography apparatus has generated each mammography image, the piece of information indicating the image taking direction thereof is appended to the image as additional information.

The observation information storage 34b is configured to store therein the observation information related to the mammography images of the patient. An observation information generating unit 35b (explained later) stores the observation information into the observation information storage 34b.

The controller 35 includes processing circuitry such as a Central Processing unit (CPU) and a memory and is configured to control operations of the image processing apparatus 30 by employing the CPU and the memory to execute various types of computer programs. More specifically, the controller 35 includes the image data obtaining unit 35a, the observation information generating unit 35b, a display controlling unit 35c, a region setting unit 35d, a position specifying unit 35e, and a transmitting unit 35f.

The image data obtaining unit 35a is configured to obtain the mammography images of the breast of the patient and the pieces of information indicating the image taking directions of the mammography images. In this situation, the image data obtaining unit 35a obtains an MLO image and a CC image for each of the left and the right breasts of the patient. More specifically, the image data obtaining unit 35a obtains the mammography images related to the patient serving as a diagnosis target and the pieces of information indicating the image taking directions of the mammography images, by communicating with the mammography apparatus 10 via the communication controller 33, and further stores the mammography images and the pieces of information indicating the image taking directions that were obtained into the image data storage 34a.

The observation information generating unit 35b is configured to generate the observation information related to the mammography images of the patient, on the basis of an observation input by the operator. More specifically, the observation information generating unit 35b receives an input of the observation related to the mammography images from a mammography examination technician via the input unit 31. Further, the observation information generating unit 35b generates the observation information indicating the received observation and stores the generated observation information into the observation information storage 34b.

The display controlling unit 35c is configured to cause the display 32 to display a reference screen used for referencing the mammography images. More specifically, when having received a display request from the operator via the input unit 31, the display controlling unit 35c reads the mammography images related to the patient serving as the diagnosis target from the image data storage 34a and reads the observation information related to the patient serving as the diagnosis target from the observation information storage 34b. Further, the display controlling unit 35c causes the display 32 to display the reference screen on which the mammography images and the observation information that were read are arranged.

The region setting unit 35d is configured to set a region of interest in at least one of the mammography images. For example, the region setting unit 35d sets a region of interest in each of the MLO and the CC images for each of the left and the right breasts of the patient. More specifically, via the input unit 31, the region setting unit 35d receives, from the operator, an operation to designate an area of an arbitrary size in an arbitrary position of each of the mammography images arranged on the reference screen displayed by the display controlling unit 35c. After that, the region setting unit 35d sets the areas designated by the operator as the regions of interest.

In this situation, for example, the region setting unit 35d may automatically detect a candidate region for a lesion from at least one of the mammography images by using a Computer Aided Diagnosis (CAD) function and may set the detected region as the region of interest. Further, for example, the region setting unit 35d may receive an operation from the operator to make an adjustment between the MLO image and the CC image with respect to the region detected by the CAD function and may set the region after the adjustment as the region of interest.

The position specifying unit 35e is configured to specify position information of each of the regions of interest in the schematic drawing that schematically expresses the breast, on the basis of pieces of position information of the regions of interest in the mammography images and the pieces of information indicating the image taking directions. More specifically, the position specifying unit 35e reads the mammography images of the patient serving as the examination target and the pieces of information indicating the image taking directions of the mammography images from the image data storage 34a and specifies the position of the region of interest in the schematic drawing on the basis of the mammography images and the pieces of information indicating the image taking directions that were read. In this situation, the schematic drawing (which may be referred to as a schema) may be a drawing of any type as long as the drawing is able to indicate positional relationships in the breast.

Figure 7:
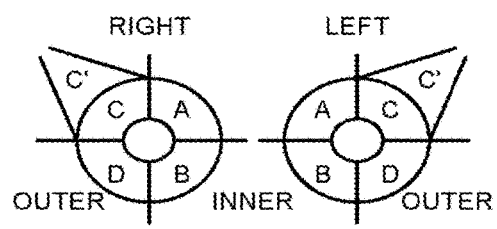
FIG. 7 is a drawing of an example of a schematic drawing used by a position specifying unit according to the first embodiment.

FIG. 7 is a drawing of an example of the schematic drawing used by the position specifying unit 35e according to the first embodiment. The example in FIG. 7 illustrates a schematic drawing of a mammary gland region, as an example of the schematic drawing that schematically expresses the breast. For example, as illustrated in FIG. 7, the schematic drawing of the mammary gland region includes, for each of the left and the right breasts, a circular region indicating the region of the breast (hereinafter, "breast region") and a substantially triangular region indicating the region of the axilla (hereinafter, "axilla region").

In this situation, each of the circular regions indicating the breast regions is divided into four regions "A" to "D", as a result of dividing in up-and-down directions and left-and-right directions. For example, the region called "A" (hereinafter, "the region A") indicates the region in the inner upper position of the breast, whereas the region called "B" (hereinafter, "the region B") indicates the region in the inner lower position of the breast. Further, for example, the region called "C" (hereinafter, "the region C") indicates the region in the outer upper position of the breast, whereas the region called "D" (hereinafter, "the region D") indicates the region in the outer lower position of the breast. Further, the substantially triangular region "C'" indicating the axilla region (hereinafter, "the region C'") extends upward diagonally from the region C and is shaped so as to become narrower as the distance from the region C increases.

Returning to the description of FIG. 6, for example, the position specifying unit 35e is configured to specify position information of each of first and second regions of interest in the schematic drawing, on the basis of position information of the first region of interest that is the region of interest in the MLO image, position information of the second region of interest that is the region of interest in the CC image, the information indicating the image taking direction of the MLO image, and the information indicating the image taking direction of the CC image. In this situation, for example, the position specifying unit 35e specifies the positions of the regions of interest in the schematic drawing, on the basis of the pieces of position information expressed in the apparatus coordinate system of the mammography apparatus that took the mammography images.

Figure 8:
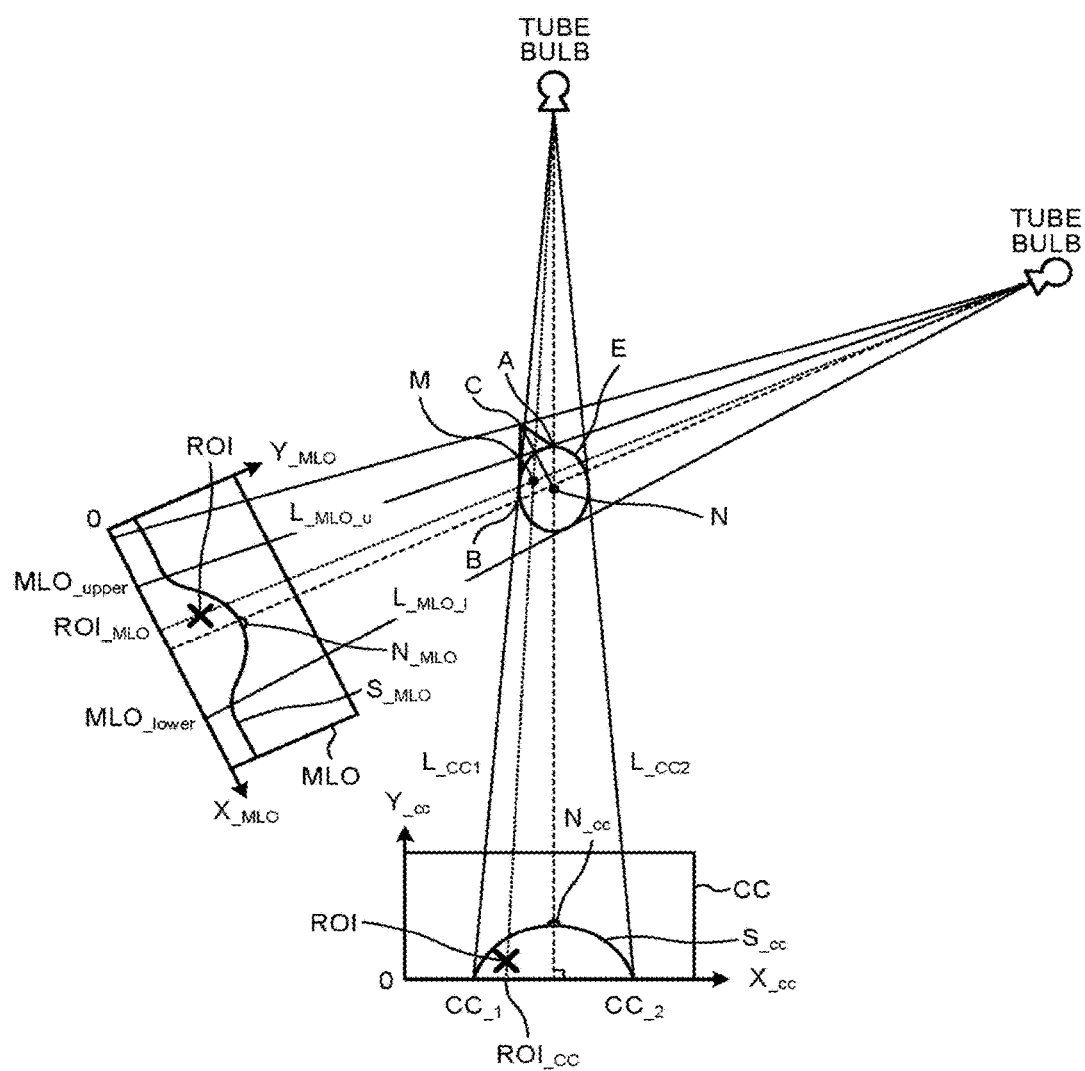
FIG. 8 is a drawing for explaining a process of specifying pieces of position information of regions of interest in a schematic drawing performed by the position specifying unit according to the first embodiment.

FIG. 8 is a drawing for explaining a process of specifying the pieces of position information of the regions of interest in the schematic drawing performed by the position specifying unit 35e according to the first embodiment. FIG. 8 illustrates an example of a method for transforming pieces of position information in the mammography images into pieces of position information in a schematic drawing, on the basis of the image taking directions expressed in the apparatus coordinates system of the mammography apparatus. In the following sections, an example will be explained in which the schematic drawing of the mammary gland region illustrated in FIG. 7 is used.

First, on the basis of the apparatus coordinate system of the mammography apparatus, the position specifying unit 35e specifies the pieces of position information of the regions corresponding to the breast region (the regions A to D) in the schematic drawing of the mammary gland region and the pieces of position information of the regions of interest set in the mammography images. For example, by using the MLO and the CC images, the position specifying unit 35e specifies the pieces of position information of the regions corresponding to the breast region and the pieces of position information of the regions of interest each of which is set in a different one of the MLO and the CC images.

First, the position specifying unit 35e sets an $X_{\_CC}$ axis, a $Y_{\_CC}$ axis, and the origin of the detector in the CC image. For example, of the two vertices positioned on the patient side among the four vertices of a rectangular detection surface of the detector, the position specifying unit 35e sets the vertex corresponding to the upper side of the breast as the origin. Further, the position specifying unit 35e detects a skin surface $S_{\_CC}$ rendered in the CC image. In this situation, as the method for detecting the skin surface $S_{\_CC}$, any of various types of generally-known image detecting methods may be used.

Further, of the two points at which the detected S cc and $X_{\_CC}$ axes are in contact with each other, the position specifying unit 35e determines the point positioned closer to the origin to be $CC_{\_1}$ and the point positioned farther from the origin to be $CC_{\_2}$. In this situation, the position specifying unit 35e may receive an operation from the operator to designate the positions of $CC_{\_1}$ and $CC_{\_2}$ out of the CC image and may set the points on the basis of the received operation. After that, the position specifying unit 35e generates a straight line $L_{\_CC1}$ with a projection from the point $CC_{\_1}$ toward the tube bulb and generates a straight line $L_{\_CC2}$ with a projection from the point $CC_{\_2}$ toward the tube bulb.

Further, the position specifying unit 35e sets an $X_{\_MLO}$ axis, a $Y_{\_MLO}$ axis, and the origin of the detector in the MLO image. For example, of the two vertices positioned on the patient side among the four vertices of a rectangular detection surface of the detector, the position specifying unit 35e sets the vertex corresponding to the outer side of the breast as the origin. Further, the position specifying unit 35e detects a skin surface $S_{\_MLO}$ rendered in the MLO image. In this situation, as the method for detecting the skin surface $S_{\_MLO}$, any of various types of generally-known image detecting methods may be used, similarly to the method for detecting the skin surface $S_{\_CC}$. After that, the position specifying unit 35e detects a breast region in the MLO image.

Figure 9:
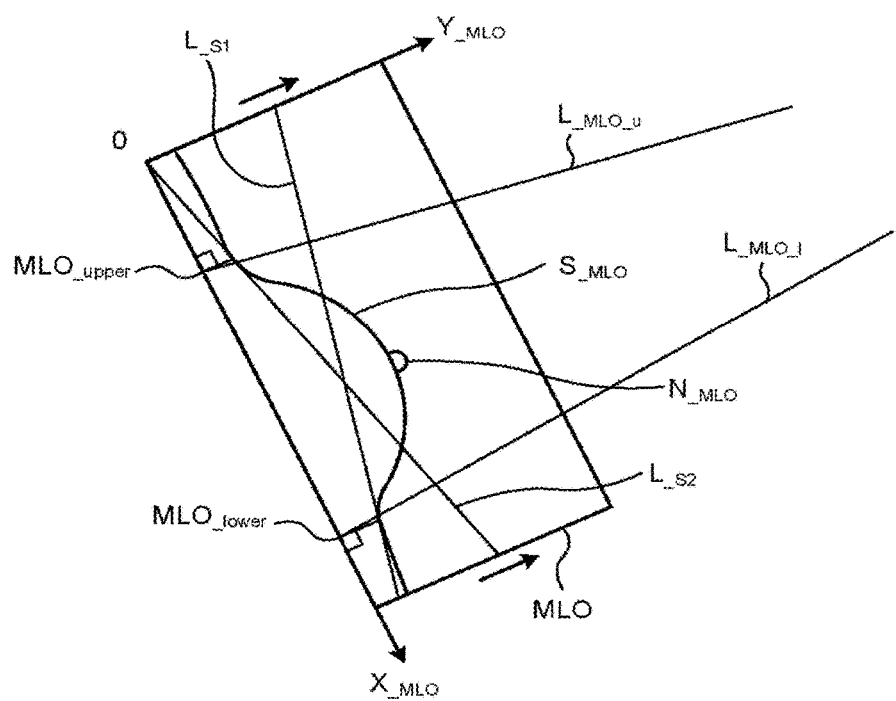
FIG. 9 is a drawing for explaining a process of detecting a breast region in a Mediolateral-Oblique (MLO) image performed by the position specifying unit according to the first embodiment.

FIG. 9 is a drawing for explaining a process of detecting the breast region in the MLO image performed by the position specifying unit 35e according to the first embodiment. As illustrated in FIG. 9, the position specifying unit 35e defines a straight line $L_{\_S1}$ expressed with a linear function $Y_{\_MLO}=aX_{\_MLO}+b$ (where a is an arbitrary positive number) and detects the point at which the straight line first intersects the skin surface $S_{\_MLO}$ by gradually increasing the value of b starting with a sufficiently small negative value. After that, the position specifying unit 35e sets the point obtained by perpendicularly projecting the detected point onto the $X_{\_MLO}$ axis as $MLO_{\_upper}$.

Further, the position specifying unit 35e defines a straight line $L_{S2}$ expressed with a linear function $Y_{\_MLO}=-aX_{\_MLO}+b$ (where a is an arbitrary positive number) and detects, in a similar manner, the point at which the straight line first intersects the skin surface $S_{\_MLO}$ by gradually increasing the value of b starting with a sufficiently small negative value. After that, the position specifying unit 35e sets the point obtained by perpendicularly projecting the detected point onto the $X_{\_MLO}$ axis as $MLO_{\_lower}$.

The values of a and b in the linear functions used above may be set to predetermined values in advance so as to be stored in the storage 34 or the like and so as to be changed in response to an instruction from the operator. Further, for example, the position specifying unit 35e may detect the position of the nipple rendered in the MLO image and may use the slope of the straight line passing through the detected nipple position and the origin of the detector as the value of a.

The position specifying unit 35e detects the region between the point $MLO_{\_upper}$ and the point $MLO_{\_lower}$ that were set in this manner as the breast region. Alternatively, the position specifying unit 35e may receive an operation from the operator to designate the positions of the point $MLO_{\_upper}$ and the point $MLO_{\_lower}$ out of the MLO image and may set the points on the basis of the received operation.

Returning to the description of FIG. 8, the position specifying unit 35e further generates a straight line $L_{\_MLO\_u}$ with a projection from the point $MLO_{\_upper}$ toward the tube bulb and generates a straight line $L_{\_MLO\_l}$ with a projection from the point $MLO_{\_lower}$ toward the tube bulb. After that, the position specifying unit 35e calculates an ellipse E inscribed in the region enclosed by the straight line $L_{\_CC1}$, the straight line $L_{\_CC2}$, the straight line $L_{\_MLO\_u}$, and the straight line $L_{\_MLO\_l}$. It should be noted that the ellipse E may be a perfect circle.

Subsequently, the position specifying unit 35e determines the point obtained by a perpendicular projection from the region of interest (ROI) set in the MLO image onto the $X_{\_MLO}$ axis to be $ROI_{\_MLO}$ and determines the point obtained by a perpendicular projection from the ROI set in the CC image onto the $X_{\_MLO}$ axis to be $ROI_{\_CC}$. Further, the position specifying unit 35e determines the region defined by causing the straight line projecting from the point $ROI_{\_MLO}$ toward the tube bulb to intersect the straight line projecting from the point $ROI_{\_CC}$ toward the tube bulb as a region M. In this situation, when the region of interest set in each of the MLO and the CC images is a point, the region M is also a point. When at least one of the regions of interest set in the MLO and the CC images is an area, the region M is a region having an area.

Further, the position specifying unit 35e sets the center position of the ellipse E as a nipple position N. Alternatively, the position specifying unit 35e may extract a nipple position $N_{\_MLO}$ from the MLO image and extract a nipple position $N_{\_CC}$ from the CC image, so as to set the intersection point between a straight line projecting from the nipple position $N_{\_MLO}$ toward the tube bulb and a straight line projecting from the nipple position $N_{\_CC}$ toward the tube bulb to be a nipple position of the ellipse E. In this situation, as the method for detecting the nipple position N, any of various types of generally-known image detecting methods may be used.

Subsequently, the position specifying unit 35e specifies position information of the region corresponding to the region C' in the schematic drawing of the mammary gland region, on the basis of the apparatus coordinate system of the mammography apparatus. For example, of the two intersection points at which a straight line passing through the tube bulb position used when the CC image was taken and the nipple position N intersects the ellipse E, the position specifying unit 35e determines the point positioned closer to the detector as a point A. Of the two intersection points at which a straight line passing through the tube bulb position used when the MLO image was taken and the nipple position N intersects the ellipse E, the position specifying unit 35e determines the point positioned closer to the detector as a point B.

Further, the position specifying unit 35e determines a point at which a straight line projecting from the origin of the $X_{\_MLO}$ axis, which is the utmost endpoint of the detector when the MLO image was taken, toward the tube bulb intersects another straight line that extends parallel to the $X_{\_MLO}$ axis and that passes through the nipple position N of the ellipse N to be a point C. After that, the position specifying unit 35e specifies the region A-B-C enclosed by the line segment connecting the point A to the point C, the line segment connecting the point B to the point C, and the ellipse E as the region corresponding to the region C'.

After that, the position specifying unit 35e specifies the position information of the region of interest in the schematic drawing by transforming the specified position information of the region of the ellipse E, the position information of the region corresponding to the region C', and the position information of the region M indicating the region of interest into pieces of position information in the schematic drawing.

Figure 10:
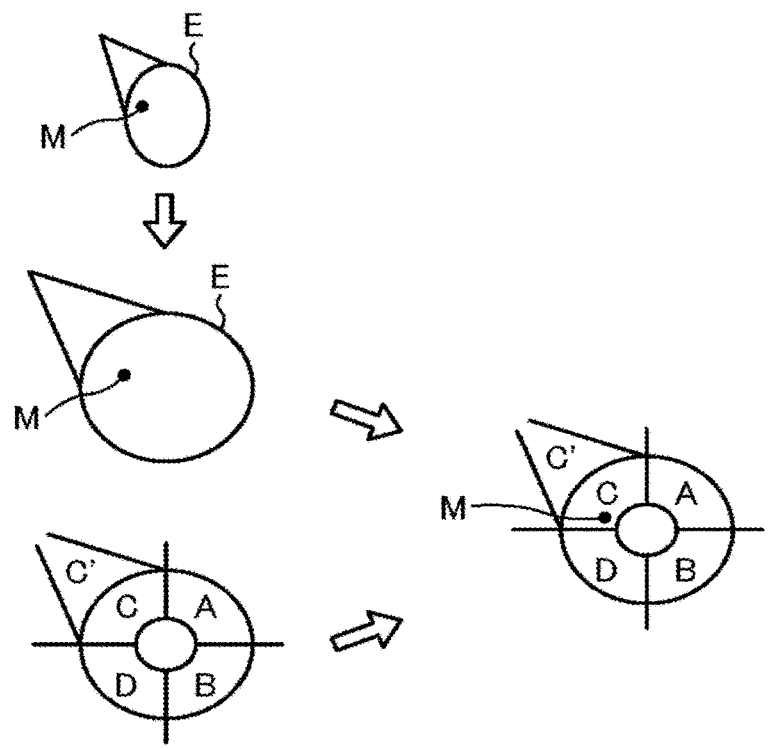
FIG. 10 is a drawing for explaining a process of specifying position information of a region of interest in a schematic drawing performed by the position specifying unit according to the first embodiment.

FIG. 10 is a drawing for explaining the process of specifying the position information of the region of interest in the schematic drawing performed by the position specifying unit 35e according to the first embodiment. For example, as illustrated in the top left and middle left sections of FIG. 10, the position specifying unit 35e transforms the pieces of position information of the regions into the pieces of position information in the schematic drawing by either enlarging or reducing the region of the ellipse E, the region corresponding to the region C', and the region M indicating the region of interest, in such a manner that each of the regions fits the shape of the schematic drawing of the mammary gland region.

First, the position specifying unit 35e transforms the position information of the region of the ellipse E into position information of the circular region indicating the breast region in the schematic drawing of the mammary gland region. In this situation, as the method for transforming the position information of the region of the ellipse E into the position information of the circular region, any of various types of generally-known coordinate transforming methods may be used. For example, the position specifying unit 35e may use a method by which position coordinates of an ellipse are transformed into position coordinates of a circle by using a predetermined transformation matrix.

Figure 11:
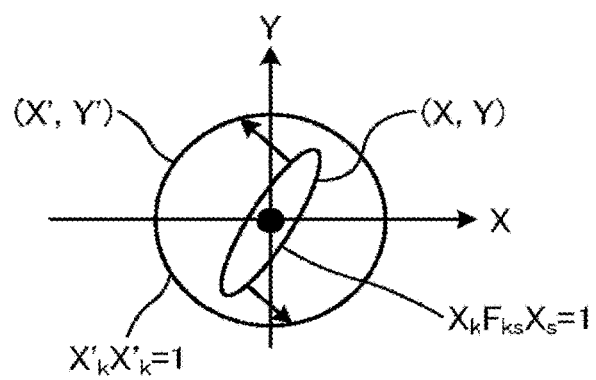
FIG. 11 is a drawing for explaining an example of a region transformation process performed by the position specifying unit according to the first embodiment.

FIG. 11 is a drawing for explaining an example of the region transformation process performed by the position specifying unit 35e according to the first embodiment. For example, as illustrated in FIG. 11, when the position coordinates of the ellipse before the transformation is expressed as $(X,Y)=(X_1,X_2)$, whereas the position coordinates of the circle after the transformation is expressed as $(X',Y')=(X_1', X_2')$, the position coordinates of the ellipse can be expressed by using Expression (1) below that uses a transformation matrix $A_{ks}$.

$$\begin{pmatrix} X_1' \\ X_2' \end{pmatrix} = \begin{pmatrix} A_{11} & A_{12} \\ A_{21} & A_{22} \end{pmatrix} \begin{pmatrix} X_1 \\ X_2 \end{pmatrix} \quad (1)$$

In this situation, when a symmetric matrix $F_{ks}$ is expressed by using b, c, and d as presented in Expression (2) below, the transformation matrix $A_{ks}$ in Expression (1) can be expressed as presented in Expression (3) below.

$$\begin{pmatrix} F_{11} & F_{12} \\ F_{21} & F_{22} \end{pmatrix} = \begin{pmatrix} b & d \\ d & c \end{pmatrix} \quad (2)$$

$$\begin{pmatrix} A_{11} & A_{12} \\ A_{21} & A_{22} \end{pmatrix} = \begin{pmatrix} \sqrt{b} & \dfrac{d}{\sqrt{b}} \\ 0 & \dfrac{\sqrt{bc-d^2}}{\sqrt{b}} \end{pmatrix} \quad (3)$$

In other words, in the present example, it is possible to transform the ellipse into the circle of a desired size, by calculating the transformation matrix $A_{ks}$ while setting the values of b, c, and d appropriately in accordance with the size of the circle after the transformation. Accordingly, by using this method, the position specifying unit 35e is able to transform the region of the ellipse E into the circular region corresponding to the breast region (the regions A to D) in the schematic drawing of the mammary gland region, by setting the values of b, c, and d appropriately in accordance with the size of the schematic drawing of the mammary gland region.

After that, the position specifying unit 35e transforms the pieces of position information of the region C' and the region M into pieces of information in the schematic drawing of the mammary gland region, by also transforming the region C' and the region M while using the same transformation matrix as the transformation matrix $A_{ks}$ used for the transformation of the ellipse E.

In this situation, for example, if no region of interest is set in the CC image, the position specifying unit 35e specifies a straight line region obtained by projecting the region of interest set in the MLO image onto the ellipse E, as a region of interest in the schematic drawing. Similarly, if no region of interest is set in the MLO image, the position specifying unit 35e specifies a straight line region obtained by projecting the region of interest set in the CC image onto the ellipse E as a region of interest in the schematic drawing.

Returning to the description of FIG. 10, after transforming the pieces of position information of the region of the ellipse E, the region corresponding to the region C', and the region M indicating the region of interest into the piece of position information in the schematic drawing, the position specifying unit 35e generates display information in which the region M indicating the region of interest is arranged in a template of the schematic drawing of the mammary gland region, on the basis of the pieces of position information of the regions in the schematic drawing, as illustrated in, for example, the bottom left and bottom right sections of FIG. 10. In this situation, the display information may be generated as image data in a format such as, for example, Joint Photographic Experts Group (JPEG), Graphics Interchange Format (GIF), or a bitmap.

After that, the position specifying unit 35e stores the generated display information into the storage 34 so as to be kept in association with the corresponding mammography image. For example, the position specifying unit 35e appends the generated display information to the mammography image as additional information and stores the display information into the image data storage 34a together with the image data of the mammography image. Alternatively, the position specifying unit 35e may store the generated display information into the image data storage 34a so as to be kept in correspondence with the patient ID assigned to the targeted patient.

For example, when the position specifying unit 35e generates the display information by using the template of the schematic drawing, the position specifying unit 35e may not only indicate the position information of the region of interest in the schematic drawing, but also display, in the schematic drawing, a region in which the mammary gland density is higher than a predetermined value, a calcified region, a tumor region, and/or the like, by extracting these regions from the mammography image. For example, the position specifying unit 35e may display the parts corresponding to these regions in the schematic drawing in colors that are different from the color of the schematic drawing and are varied for the different types of regions or may display marks that are determined in advance for the different types of regions.

The display information generated by the position specifying unit 35e in this manner is transmitted to either the image display apparatus 40 or the ultrasound diagnosis apparatus 20 by, for example, the transmitting unit 35f (explained later). After that, the image display apparatus 40 or the ultrasound diagnosis apparatus 20 that received the display information outputs the position information of the region of interest in the schematic drawing to the display 32 in a predetermined display format thereof, on the basis of the received display information.

For example, the image display apparatus 40 or the ultrasound diagnosis apparatus 20 outputs the position information of the region of interest in the schematic drawing, as reference information used during an ultrasound diagnosis process. Further, for example, the image display apparatus 40 or the ultrasound diagnosis apparatus 20 outputs the position information in the schematic drawing that corresponds to the patient ID of a patient who is currently undergoing an ultrasound diagnosis process.

Figure 12:
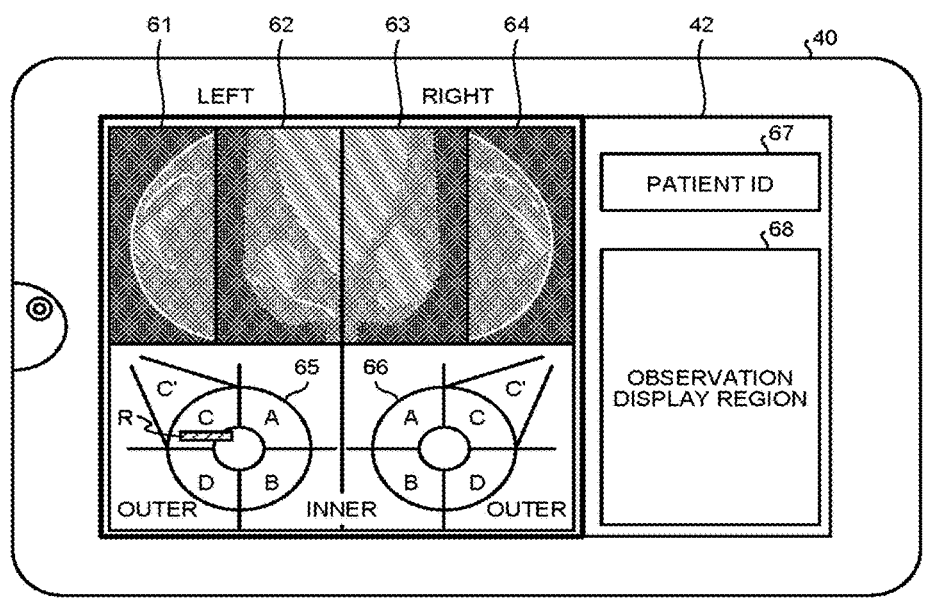
FIG. 12 is a drawing of an example of display information displayed by an image display apparatus according to the first embodiment.

FIG. 12 is a drawing of an example of the display information displayed by the image display apparatus 40 according to the first embodiment. For example, as illustrated in FIG. 12, the image display apparatus 40 causes a display 42 to display a reference screen on which mammography images 61 to 64, mammary gland region schematic drawings 65 and 66, a patient ID region 67, and an observation display region 68 are arranged.

In this situation, for example, the mammography image 61 is a CC image related to the left breast of the patient. The mammography image 62 is an MLO image related to the left breast of the patient. The mammography image 63 is an MLO image related to the right breast of the patient. The mammography image 64 is a CC image related to the right breast of the patient. Further, the patient ID region 67 is a region used for displaying the patient ID. The observation display region 68 is a region used for displaying observation information related to the mammography images of the patient.

Further, the schematic drawing 65 indicates a mammary gland region of the left breast of the patient. The schematic drawing 66 indicates a mammary gland region of the right breast of the patient. In this situation, each of the schematic drawings 65 and 66 is a schematic drawing of a mammary gland region displayed on the basis of the display information transmitted from the image display apparatus 40 and, for example, a rectangular mark R indicating the region of interest is displayed in one of the schematic drawings.

Returning to the description of FIG. 6, the transmitting unit 35f is configured to transmit the display information generated by the position specifying unit 35e either to the image display apparatus 40 or the ultrasound diagnosis apparatus 20, in response to an instruction from the operator. More specifically, the transmitting unit 35f receives a display information transmission instruction from the operator of either the image display apparatus 40 or the ultrasound diagnosis apparatus 20 via the input unit 31. Further, when having received the display information transmission instruction, the transmitting unit 35f reads the display information designated by the operator from the storage 34 and transmits the read display information to either the image display apparatus 40 or the ultrasound diagnosis apparatus 20.

In this situation, for example, in response to a request from either the image display apparatus 40 or the ultrasound diagnosis apparatus 20, the transmitting unit 35f may transmit the display information generated by the position specifying unit 35e to either the image display apparatus 40 or the ultrasound diagnosis apparatus 20. In that situation, for example, the transmitting unit 35f receives the request for the display information from either the image display apparatus 40 or the ultrasound diagnosis apparatus 20 via the communication controller 33. After that, when having received the request for the display information, the transmitting unit 35f reads the requested display information from the storage 34. For example, when the display information is stored in the storage 34 while being kept in correspondence with the patient ID, the transmitting unit 35f receives a patient ID as the request from the image display apparatus 40 or the ultrasound diagnosis apparatus 20, so as to read the display information kept in correspondence with the received patient ID. After that, the transmitting unit 35f transmits the read display information to either the image display apparatus 40 or the ultrasound diagnosis apparatus 20 that transmitted the request.

Figure 13:
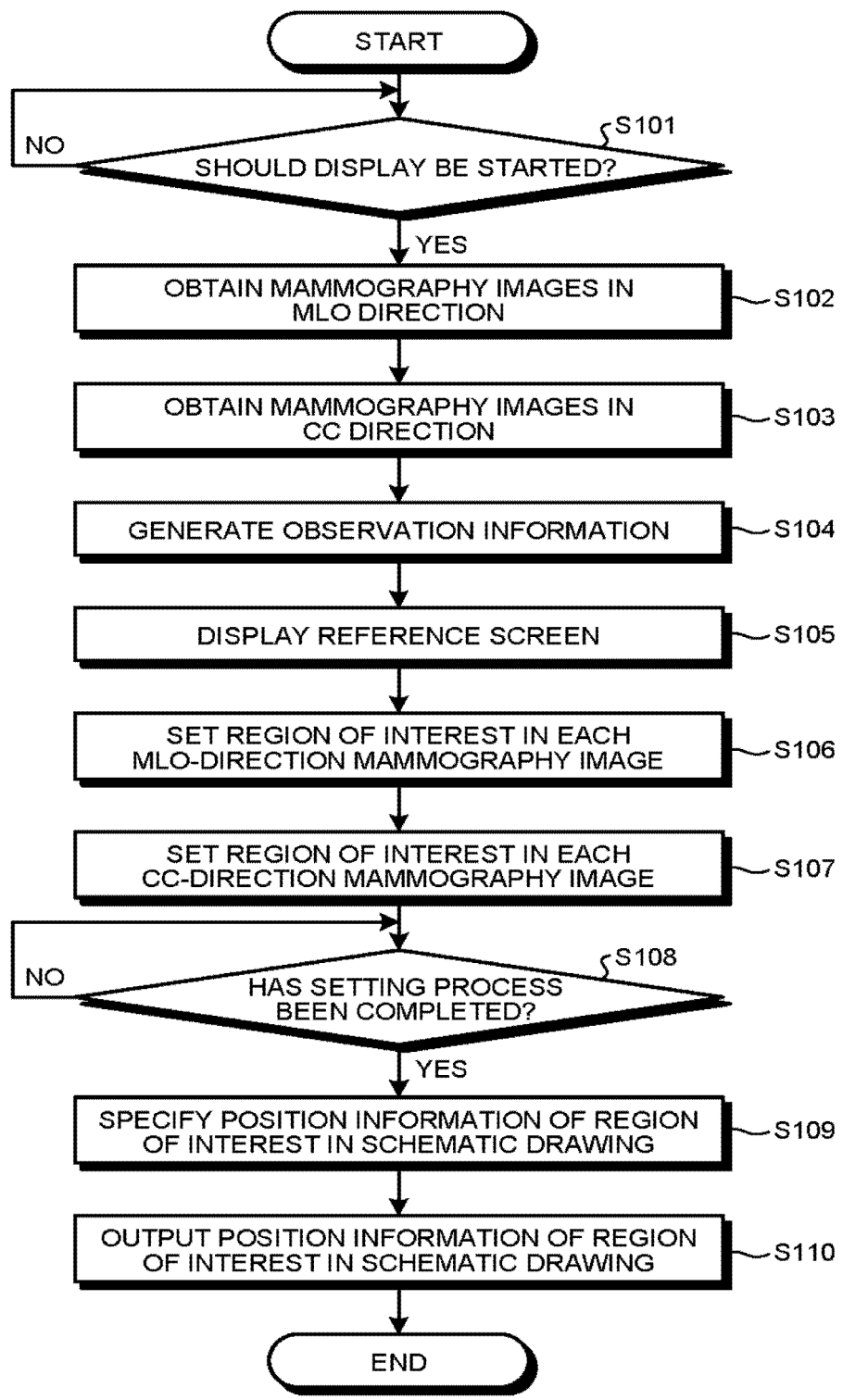
FIG. 13 is a flowchart of a processing procedure of a process performed by an image processing apparatus according to the first embodiment.

FIG. 13 is a flowchart of a processing procedure of a process performed by the image processing apparatus 30 according to the first embodiment. As illustrated in FIG. 13, when the image processing apparatus 30 has received an instruction to display mammography images and observation information from the operator (step S101: Yes), the image data obtaining unit 35a obtains a mammography image in an MLO direction and a mammography image in a CC direction for each of the left and the right breasts of the patient (steps S102 and S103). Further, the observation information generating unit 35b generates observation information related to the breast of the patient (step S104).

Subsequently, the display controlling unit 35c causes the display 32 to display a reference screen used for referencing the mammography images (step S105). After that, via the input unit 31, the region setting unit 35d receives, from the operator, an operation to designate a desired area in at least one of the MLO-direction mammography images arranged on the reference screen and sets the designated area as a region of interest (step S106). Further, via the input unit 31, the region setting unit 35d receives, from the operator, an operation to designate a desired area in at least one of the CC-direction mammography images arranged on the reference screen and sets the designated area as a region of interest (step S107).

Further, when the region of interest has been set in each of the MLO-direction and CC-direction mammography images (step S108: Yes), the position specifying unit 35e specifies position information of the region of interest in the schematic drawing, on the basis of the pieces of information of the regions of interest that were set in the images and the pieces of information indicating the image taking directions of the images (step S109). After that, the position specifying unit 35e outputs the specified position information of the region of interest in the schematic drawing to, for example, the image display apparatus 40, the ultrasound diagnosis apparatus 20, or the like (step S110).

Modification Examples of First Embodiment

In the first embodiment described above, the example is explained in which the position specifying unit 35e specifies the position of the region of interest in the schematic drawing, on the basis of the position information expressed in the apparatus coordinate system of the mammography apparatus that took the mammography images. However, possible embodiments are not limited to this example. For instance, the position specifying unit 35e may specify the position information of the region of interest in the schematic drawing by performing a predetermined image processing process on the mammography images.

Figure 14:
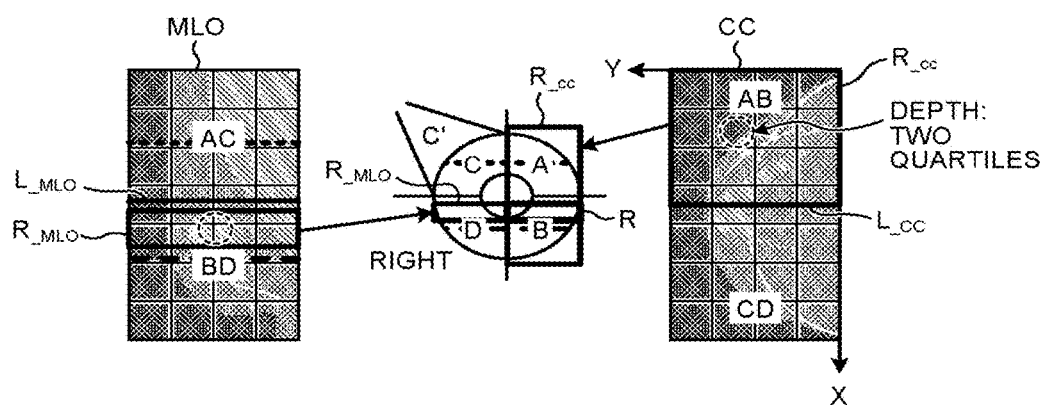
FIG. 14 is a drawing for explaining a process of specifying position information of a region of interest in a schematic drawing performed by a position specifying unit according to a modification example of the first embodiment.

FIG. 14 is a drawing for explaining a process of specifying position information of a region of interest in a schematic drawing performed by the position specifying unit 35e according to a modification example of the first embodiment. For example, as illustrated in FIG. 14, the position specifying unit 35e divides an MLO image into a region on the abdomen side and a region on the head side by using a straight line $L\_{MLO}$ passing through the nipple. Further, the position specifying unit 35e sets a region that is positioned parallel to the straight line $L\_{MLO}$ and that has a width to include the region of interest (the circular region indicated with a broken line in FIG. 14) set in the MLO image, as a region $R\_{MLO}$.

Further, the position specifying unit 35e divides a CC image into an inner region (the region corresponding to the region AB) and an outer region (the region corresponding to the region CD) by using a straight line $L\_{CC}$ passing through the nipple. Further, of the two regions resulting from the division, the position specifying unit 35e sets a region including the region of interest (the circular region indicated with a broken line in FIG. 14) set in the CC image as a region $R\_{CC}$.

After that, on the basis of pieces of information of the region $R\_{MLO}$ and the region $R\_{CC}$, the position specifying unit 35e specifies position information of the overlapping section between the region $R\_{MLO}$ and the region $R\_{CC}$ in the schematic drawing. Further, the position specifying unit 35e generates display information in which the overlapping section between the region $R\_{MLO}$ and the region $R\_{CC}$ is arranged in a template of the schematic drawing of the mammary gland region, on the basis of the specified position information.

In this situation, when generating the display information by using the template of the schematic drawing, for example, the position specifying unit 35e may further display depth information of the region of interest, as position information of the region of interest in the schematic drawing. For example, the position specifying unit 35e divides a CC image equally in the Y direction into N sections (where N is an arbitrary integer) and displays the position of the region of interest by using an N-quantile method. In one example, for instance, the position specifying unit 35e divides the CC image equally in the Y direction into four sections and, if the region of interest is set in the second section from the opposite side of the chest wall, the position specifying unit 35e displays the position as "two quartiles".

As explained above, in the first embodiment, the image processing apparatus 30 sets the regions of interest in the mammography images of the breast of the patient and specifies and outputs the position information of the region of interest in the schematic drawing that schematically expresses the breast, on the basis of the pieces of position information of the regions of interest in the mammography images and the pieces of information indicating the image taking directions of the mammography images. This arrangement makes it possible, for example, for the mammography examination technician to set the regions of interest in the mammography images by using the image processing apparatus 30 and for the ultrasound examination technician to easily understand, by using either the image display apparatus 40 or the ultrasound diagnosis apparatus 20, the position in the schematic drawing corresponding to the regions of interest set by the mammography examination technician. It is therefore possible to improve the level of precision of the mammary gland image diagnosis process.

Figure 15:
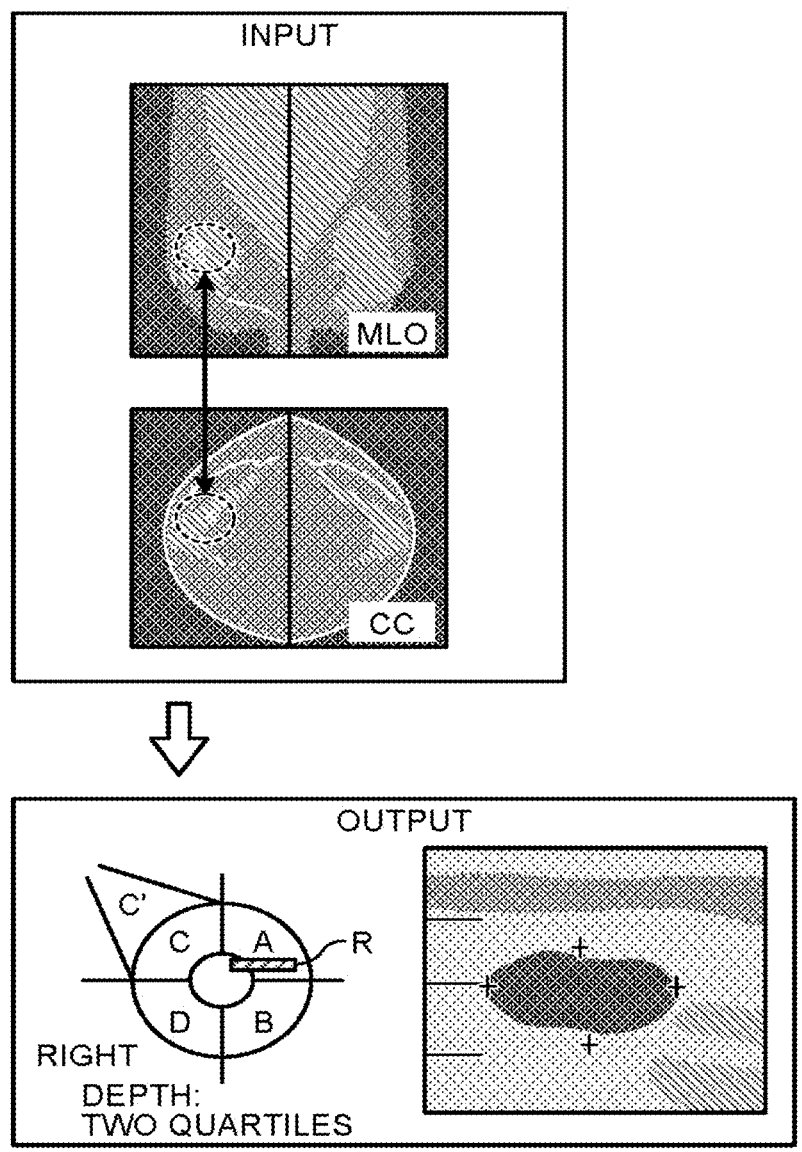
FIG. 15 is a drawing for explaining a relationship between mammography images and a schematic drawing according to the first embodiment.

FIG. 15 is a drawing for explaining a relationship between mammography images and a schematic drawing according to the first embodiment. For example, as illustrated in FIG. 15, there may be some situations where it is difficult to understand from only looking at the mammography images, to which position the regions of interest (the circular regions indicated with broken lines in FIG. 15) set in the MLO and the CC images correspond, when an ultrasound imaging process is performed on the breast. Even in those situations, according to the first embodiment, the mark R indicating the region of interest is displayed in the schematic drawing that schematically expresses the breast, the ultrasound examination technician is able to easily understand the position in the breast that needs to be examined during the ultrasound diagnosis process.

In the first embodiment above, the example is explained in which the region of interest is displayed in the schematic drawing, on the basis of the region of interest set in each of the MLO and the CC images; however, possible embodiments are not limited to this example. For instance, it is known that during an image taking process performed by a mammography apparatus, a blind area may occur due to the curve of the chest wall and a relationship between fixed tissues and movable tissues. When a lesion is present in such a blind area, there may be some situations where no region of interest is set in a mammography image.

Figure 16:
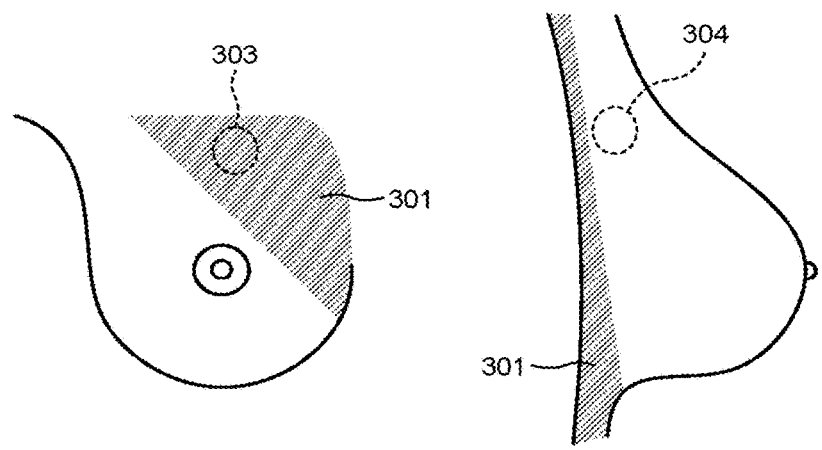
FIG. 16 is a drawing illustrating a blind area in an MLO image taking process.
Figure 17:
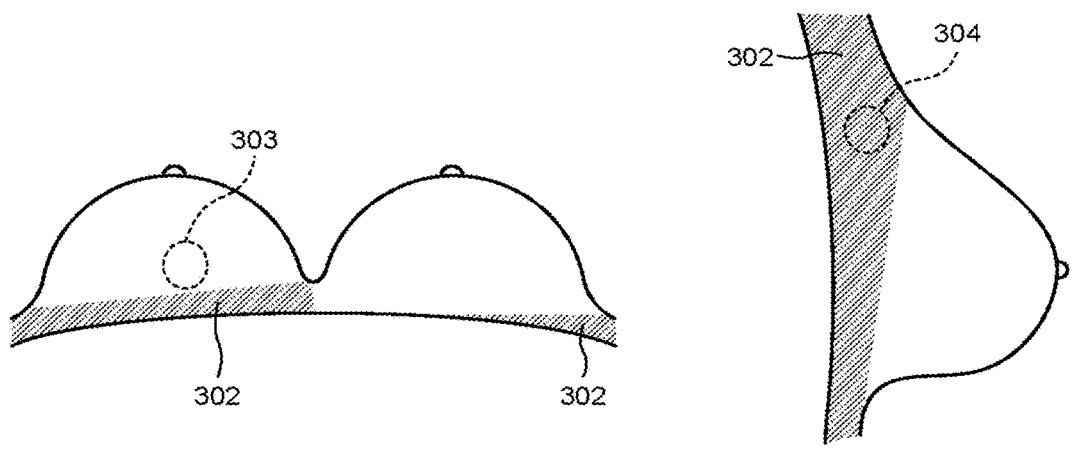
FIG. 17 is a drawing illustrating a blind area in a Cranio-Caudal (CC) image taking process.

FIG. 16 is a drawing illustrating a blind area in an MLO image taking process. FIG. 17 is a drawing illustrating a blind area in a CC image taking process. For example, as illustrated in FIG. 16, during MLO image taking processes, a blind area 301 can easily occur in an upper inner part (see the left section of FIG. 16) and a lower part (see the right section of FIG. 16) of the breast. Further, for example, as illustrated in FIG. 17, during CC image taking processes, a blind area 302 can easily occur in an upper part of the breast (see the right section of FIG. 17) and an outer part positioned closer to the axilla (see the left section of FIG. 17).

In this situation, for example, if a lesion is present in a blind area occurring during an MLO or CC image taking process, there may be some situations where no region of interest is set in at least one of the MLO and the CC images. For example, as illustrated in the left section of FIG. 16, if a lesion 303 is present in the blind area in the upper inner part of the breast, there may be some situations where the lesion 303 is not rendered in the MLO image and, as a result, no region of interest is set in the MLO image. As another example, as illustrated in the right section of FIG. 17, if a lesion 304 is present in the blind area in the upper part of the breast, there may be some situations where the lesion 304 is not rendered in the CC image, and as a result, no region of interest is set in the CC image.

To cope with this situation, for example, when no region of interest is set in at least one of the MLO and the CC images, it is also acceptable to further cause information indicating the blind area to be displayed in the schematic drawing of the breast. In that situation, for example, the image processing apparatus 30 is configured so that the position specifying unit 35e further specifies whether a blind area is occurring or not, on the basis of the mammography images. Further, on the basis of the specified result, the position specifying unit 35e generates display information indicating position information of the blind area in the schematic drawing, in addition to the position information of the region of interest in the schematic drawing. Further, for example, on the basis of the display information generated by the position specifying unit 35e, either the image display apparatus 40 or the ultrasound diagnosis apparatus 20 further outputs the position information of the blind area in the schematic drawing, together with the position information of the region of interest in the schematic drawing.

For example, when specifying the region of interest by using the method indicated in FIGS. 8 to 11, the position specifying unit 35e at first detects whether or not a region of interest is set in each of the MLO and the CC images. After that, if a region of interest is set in the CC image, but no region of interest is set in the MLO image, the position specifying unit 35e specifies that a blind area is occurring in the MLO image. On the contrary, if a region of interest is set in the MLO image, but no region of interest is set in the CC image, the position specifying unit 35e specifies that a blind area is occurring in the CC image.

After that, on the basis of the specified result, the position specifying unit 35e generates display information in which the position information of the blind area is displayed together with the position information of the region of interest, in the template of the schematic drawing of the mammary gland region.

Figure 18:
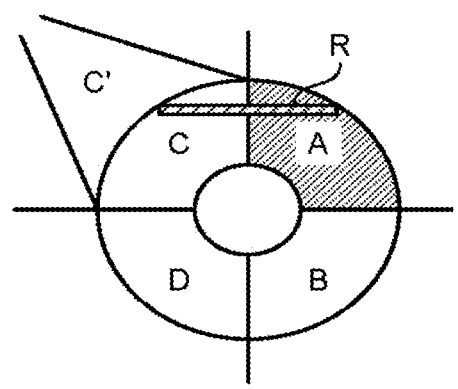
FIG. 18 is a first drawing for explaining a display of a blind area realized by the position specifying unit according to another modification example of the first embodiment.
Figure 19:
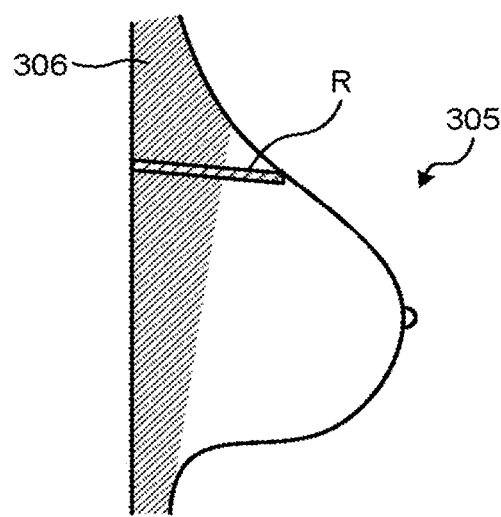
FIG. 19 is a second drawing for explaining the display of the blind area realized by the position specifying unit according to the modification example of the first embodiment.

FIGS. 18 and 19 are drawings for explaining a display of a blind area realized by the position specifying unit 35e according to another modification example of the first embodiment. For example, when having specified that a blind area is occurring in an MLO image, the position specifying unit 35e displays the region A in the schematic drawing illustrated in FIG. 7 by using a display mode different from the display mode used for the other regions, as illustrated in FIG. 18. In that situation, for example, the position specifying unit 35e may display the region A in a color different from the color of the other regions or with a pattern different from the pattern of the other regions. Although FIG. 18 illustrates the example in which the display mode used for the entirety of the region A is arranged to be different, it is also acceptable to, for example, arrange the display mode of only a part of the region A to be different. For example, it is acceptable to arrange the display mode of a part positioned close to an outer circumferential part of the region A to be different.

In this situation, as mentioned above, in the first embodiment, if no region of interest is set in the MLO image, the position specifying unit 35e specifies a straight line region obtained by projecting the region of interest set in the CC image, as a region of interest in the schematic drawing. As a result, for example, as illustrated in FIG. 18, the straight-line-shaped region of interest R is displayed in the schematic drawing. This type of display, for example, makes it possible for an ultrasound examination technician to determine that it is necessary to perform an ultrasound examination especially carefully on the part corresponding to the region A, within the straight-line-shaped region of interest R.

Further, for example, when having specified that a blind area is occurring in a CC image, the position specifying unit 35e uses, as illustrated in FIG. 19, a template 305 of a schematic drawing shaped as a lateral view of the breast, in place of the schematic drawing illustrated in FIG. 7. In this situation, for example, the position specifying unit 35e uses a schematic drawing of the right breast if the blind area is occurring in the CC image of the right breast and uses a schematic drawing of the left breast if the blind area is occurring in the CC image of the left breast. In that situation, for example, the schematic drawing of the right breast and the schematic drawing of the left breast are defined to have shapes that are symmetrical to each other in the left-and-right direction.

Further, in the template 305 of the schematic drawing, the position specifying unit 35e generates display information indicating a region expressing a general shape of a blind area expected during CC image taking processes, together with the position information of the region of interest. For example, in the schematic drawing, the position specifying unit 35e displays a region 306 indicating a blind area occurring in an upper part of the breast by using a display mode different from the display mode used for the other region. In that situation, for example, the position specifying unit 35e displays the region 306 in a color different from the color of the other region or with a pattern different from the pattern of the other region.

In this situation, as mentioned above, in the first embodiment, if no region of interest is set in the CC image, the position specifying unit 35e specifies a straight line region obtained by projecting the region of interest set in the MLO image, as a region of interest in the schematic drawing. As a result, for example, as illustrated in FIG. 19, the straight-line-shaped region of interest R is displayed in the schematic drawing. This type of display, for example, makes it possible for an ultrasound examination technician to determine that it is necessary to perform an ultrasound examination especially carefully on the side positioned closer to the upper part of the breast, within the straight-line-shaped region of interest R.

In the description above, the example is explained in which, when no region of interest is set in one of the MLO and the CC images, the position specifying unit 35e automatically displays the position information of the blind area in the schematic drawing. However, possible embodiments are not limited to this example. For instance, the position specifying unit 35e may display the region to be displayed as a blind area, on the basis of an instruction from the operator. In that situation, for example, when no region of interest is set in one of the MLO and the CC images, the position specifying unit 35e receives, from the operator, an operation to designate the area of the region to be displayed as the blind area, in the mammography image in which no region of interest is set. After that, on the basis of the area designated by the operator, the position specifying unit 35e displays the blind area in the template of the schematic drawing.

In the description above, the example is explained in which the blind area is displayed in the schematic drawing of the breast when no region of interest is set in at least one of the MLO and the CC images; however, possible embodiments are not limited to this example.

For instance, the position specifying unit 35e may specify the position information of the region of interest in the schematic drawing, on the basis of a region of interest set only in one of the MLO and the CC images. In that situation, for example, when specifying the region of interest by using the method illustrated in FIG. 14, the position specifying unit 35e at first detects whether or not a region of interest is set in each of the MLO and the CC images. After that, in accordance with the detection result of the region of interest, the position specifying unit 35e generates display information in which the one or more regions of interest are arranged in the schematic drawing.

Figure 20:
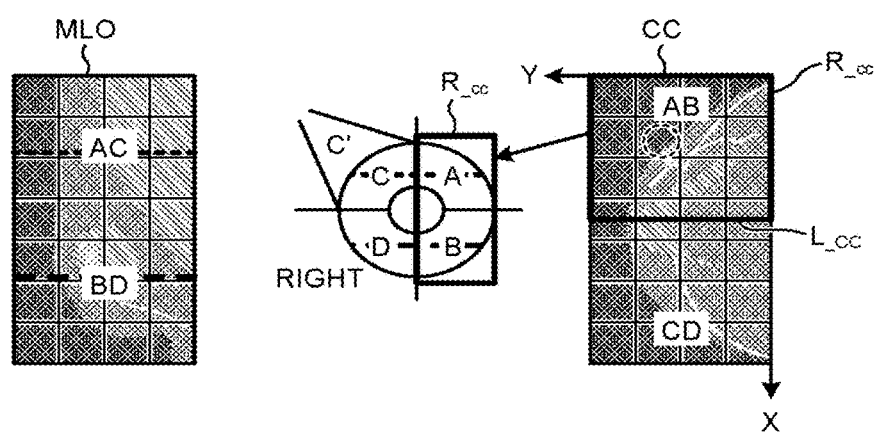
FIG. 20 is a first drawing for explaining a process of specifying position information of a region of interest in a schematic drawing according to yet another modification example of the first embodiment.
Figure 21:
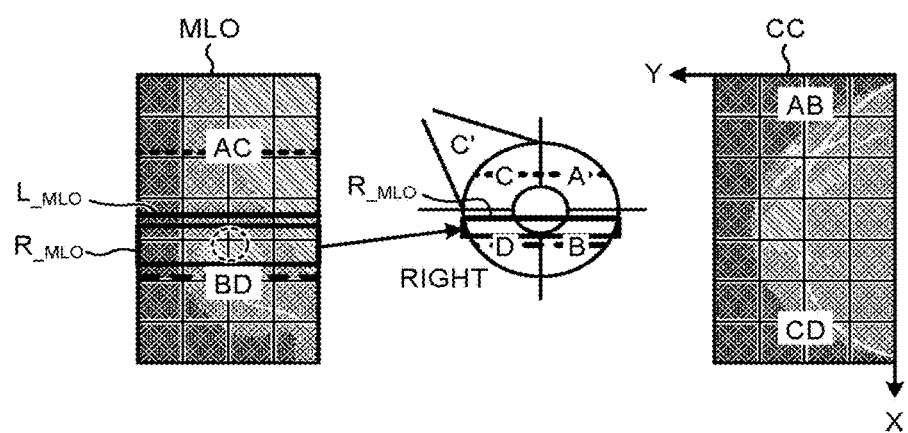
FIG. 21 is a second drawing for explaining the process of specifying the position information of the region of interest in the schematic drawing according to the modification example of the first embodiment.

FIGS. 20 and 21 are drawings for explaining a process of specifying position information of a region of interest in a schematic drawing according to yet another modification example of the first embodiment. For example, when a region of interest (the circular region indicated with a broken line in FIG. 20) is set in a CC image, but no region of interest is set in an MLO image, the position specifying unit 35e divides the CC image, as illustrated in FIG. 20, into an inner region (the region corresponding to the region AB) and an outer region (the region corresponding to the region CD) by using a straight line $L_{\_CC}$ passing through the nipple and further sets, of the two regions resulting from the division, the region including the region of interest set in the CC image, as a region $R_{\_CC}$. Further, the position specifying unit 35e specifies position information of the region $R_{\_CC}$ in the schematic drawing, on the basis of position information of the region $R_{\_CC}$ expressed in the apparatus coordinate system of the mammography apparatus. After that, the position specifying unit 35e generates display information in which the region $R_{\_CC}$ is arranged in a template of the schematic drawing of the mammary gland region, on the basis of the specified position information. For example, when the region of interest is set in the inner region of the CC image, the position specifying unit 35e displays a frame indicating the region $R_{\_CC}$ serving as the region of interest, in the region AB of the schematic drawing. As another example, when the region of interest is set in the outer region of the CC image, the position specifying unit 35e displays a frame indicating the region $R_{\_CC}$ serving as the region of interest, in the region CD of the schematic drawing.

In another example, when a region of interest (the circular region indicated with a broken line in FIG. 21) is set in an MLO image, but no region of interest is set in a CC image, the position specifying unit 35e divides the MLO image, as illustrated in FIG. 21, into an abdomen-side region and a head-side region by using a straight line $L_{\_MLO}$ passing through the nipple. Further, the position specifying unit 35e sets a region that is positioned parallel to the straight line $L_{\_MLO}$ and that has a width to include the region of interest (the circular region indicated with a broken line in FIG. 21) set in the MLO image, as a region $R_{\_MLO}$. Further, the position specifying unit 35e specifies position information of the region $R_{\_MLO}$ in the schematic drawing, on the basis of position information of the region $R_{\_MLO}$. After that, the position specifying unit 35e generates display information in which the region $R_{\_MLO}$ is arranged in a template of the schematic drawing of the mammary gland region, on the basis of the specified position information. Alternatively, the position specifying unit 35e may set the entirety of a region, either the abdomen-side region or the head-side region, that includes the region of interest set in the MLO image, as the region $R_{\_MLO}$. For example, when the region of interest is set in the abdomen-side region of the MLO image, the position specifying unit 35e displays a frame indicating the region $R_{\_MLO}$ serving as the region of interest, in the region DB of the schematic drawing. As another example, when the region of interest is set in the head-side region of the MLO image, the position specifying unit 35e displays a frame indicating the region $R_{\_MLO}$ serving as the region of interest, in the region AC of the schematic drawing.

As explained above, even when no region of interest is set in one of the MLO and the CC images, the position specifying unit 35e specifies the position information of the region of interest in the schematic drawing, on the basis of the one of the mammography images in which the region of interest is set. With this arrangement, even if a blind area is occurring in either the MLO image or the CC image, because the position of the region of interest set in at least one of the mammography images is indicated in the schematic drawing, it is possible to assist the ultrasound examination technician.

Second Embodiment

In the first embodiment above, the example is explained in which the image processing apparatus 30 sets the one or more regions of interest in the mammography images and specifies the position information of the region of interest in the schematic drawing. In contrast, in a second embodiment, an example will be explained in which the image display apparatus 40 sets one or more regions of interest in mammography images and specifies the position information of the region of interest in a schematic drawing. The configurations of the apparatuses included in a medical information processing system according to the second embodiment are the same as those illustrated in FIG. 1.

Figure 22:
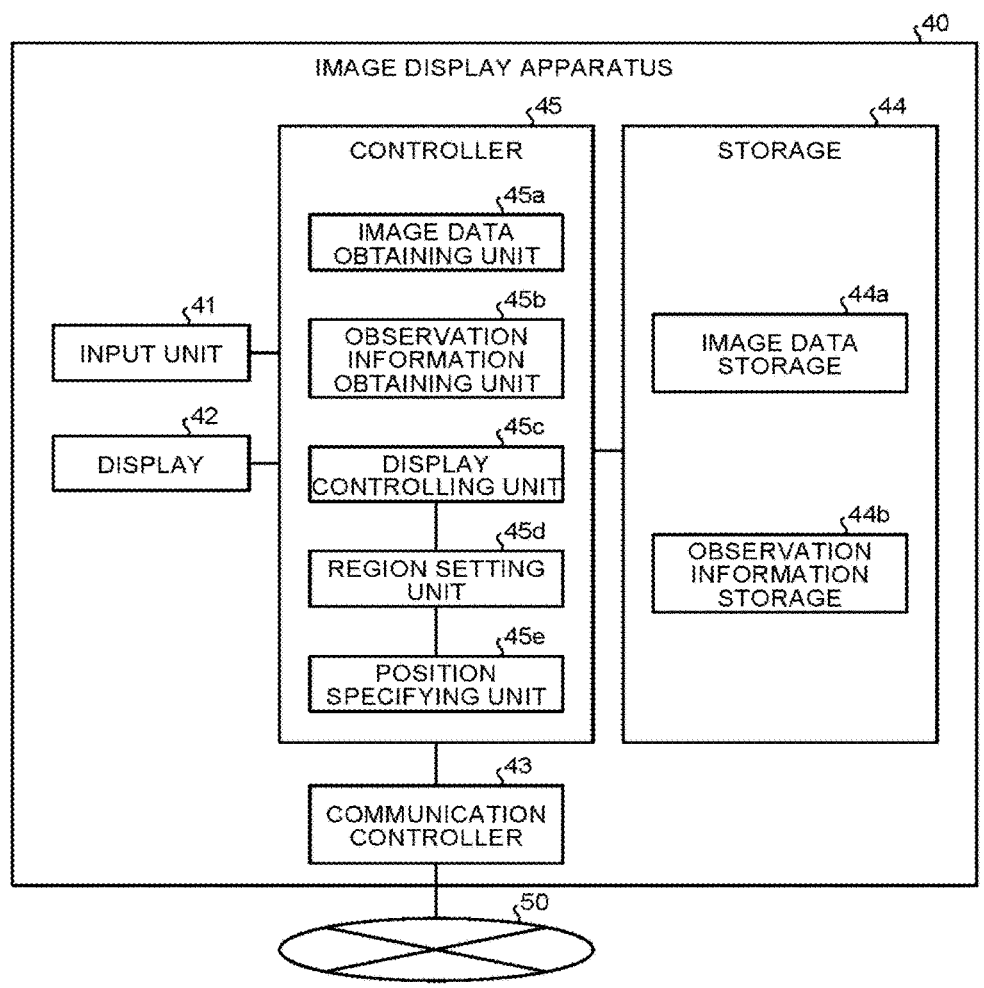
FIG. 22 is a diagram of an exemplary configuration of an image display apparatus according to a second embodiment.

FIG. 22 is a diagram of an exemplary configuration of the image display apparatus 40 according to the second embodiment. As illustrated in FIG. 22, the image display apparatus 40 includes an input unit 41, a display 42, a communication controller 43, a storage 44, and a controller 45.

The input unit 41 is configured to receive inputs of various types of operations and various types of information from an operator. For example, the input unit 41 may be configured by using a button, a touch panel, and/or a pen tablet.

The display 42 is configured to display a GUI used for receiving the various types of operations from the operator and various types of images. For example, the display 42 may be configured by using a liquid crystal display device or a touch panel.

The communication controller 43 is configured to control communication performed with another apparatus via the network 50. For example, the communication controller 43 may perform wireless communication with the other apparatus by connecting to the network 50 via a wireless LAN.

The storage 44 is a storage device such as a hard disk, a semiconductor memory, or the like and is configured to store various types of information therein. More specifically, the storage 44 includes an image data storage 44a and an observation information storage 44b.

The image data storage 44a is configured to store therein mammography images of the breast of the patient and information indicating the image taking directions of the mammography images. More specifically, similarly to the image data storage 34a described in the first embodiment, the image data storage 44a stores therein the mammography images and the pieces of information each of which indicates an image taking direction and is kept in association with a corresponding one of the images. An image data obtaining unit 45a (explained later) stores the mammography images into the image data storage 44a.

The observation information storage 44b is configured to store therein the observation information related to the mammography images of the patient. An observation information obtaining unit 45b (explained later) stores the observation information into the observation information storage 44b.

The controller 45 includes processing circuitry such as a CPU and a memory and is configured to control operations of the image display apparatus 40 by employing the CPU and the memory to execute various types of computer programs. More specifically, the controller 45 includes the image data obtaining unit 45a, the observation information obtaining unit 45b, a display controlling unit 45c, a region setting unit 45d, and a position specifying unit 45e.

The image data obtaining unit 45a is configured to obtain the mammography images of the breast of the patient and the pieces of information indicating the image taking directions of the mammography images. In this situation, the image data obtaining unit 45a obtains a mammography image in an MLO direction and a mammography image in a CC direction for each of the left and the right breasts of the patient.

More specifically, the image data obtaining unit 45a obtains the mammography images related to the patient serving as a diagnosis target and the pieces of information indicating the image taking directions of the mammography images, by communicating with the image processing apparatus 30 via the communication controller 43, and further stores the mammography images and the pieces of information indicating the image taking directions that were obtained into the image data storage 44a. Alternatively, the image data obtaining unit 45a may obtain the mammography images related to the patient serving as the diagnosis target and the pieces of information indicating the image taking directions of the mammography images, by communicating with the mammography apparatus 10 via the communication controller 43.

The observation information obtaining unit 45b is configured to obtain the observation information related to the breast of the patient. More specifically, the observation information obtaining unit 45b obtains the observation information of the mammography images related to the patient serving as the diagnosis target by communicating with the image processing apparatus 30 via the communication controller 43. Further, the observation information obtaining unit 45b stores the obtained observation information into the observation information storage 44b.

The display controlling unit 45c is configured to cause the display 42 to display a reference screen used for referencing the mammography images. More specifically, when having received a display request from the operator via the input unit 41, the display controlling unit 45c reads the mammography images related to the patient serving as the diagnosis target from the image data storage 44a and reads the observation information related to the patient serving as the diagnosis target from the observation information storage 44b. Further, the display controlling unit 45c causes the display 42 to display the reference screen on which the mammography images and the observation information that were read are arranged.

The region setting unit 45d is configured to set a region of interest in at least one of the mammography images. More specifically, by using the same method as the one used by the region setting unit 35d described in the first embodiment, the region setting unit 45d sets the region of interest in at least one of the mammography images. For example, the region setting unit 45d sets a region of interest in each of the MLO and the CC images for each of the left and the right breasts of the patient.

The position specifying unit 45e is configured to specify position information of each of the regions of interest in the schematic drawing that schematically expresses the breast, on the basis of pieces of position information of the regions of interest in the mammography images and the pieces of information indicating the image taking directions. More specifically, the position specifying unit 45e specifies the position information of each of the regions of interest in the schematic drawing by using the same method as the one used by the position specifying unit 35e described in the first embodiment.

After that, similarly to the position specifying unit 35e described in the first embodiment, the position specifying unit 45e generates display information in which a region indicating the region of interest is arranged in a template of the schematic drawing of the mammary gland region. After that, for example, the position specifying unit 45e causes the display 42 to display the reference screen illustrated in FIG. 12, on the basis of the generated display information.

As explained above, in the second embodiment, the image display apparatus 40 sets the regions of interest in the mammography images of the breast of the patient and specifies and outputs the position of the region of interest in the schematic drawing that schematically expresses the breast, on the basis of the pieces of position information of the regions of interest in the mammography images and the pieces of information indicating the image taking directions of the mammography images. This arrangement makes it possible, for example, for the ultrasound examination technician to easily understand, by using the image display apparatus 40, the position in the schematic drawing corresponding to the regions of interest set in the mammography images. It is therefore possible to improve the level of precision of the mammary gland image diagnosis.

Third Embodiment

In the first and the second embodiments described above, the example is explained in which either the image processing apparatus 30 or the image display apparatus 40 sets the regions of interest in the mammography images and specifies the position information of the region of interest in the schematic drawing. In contrast, in a third embodiment, an example will be explained in which the ultrasound diagnosis apparatus 20 sets regions of interest in mammography images and specifies position information of the region of interest in a schematic drawing. The configurations of the apparatuses included in a medical information processing system according to the third embodiment are the same as those illustrated in FIG. 1.

Figure 23:
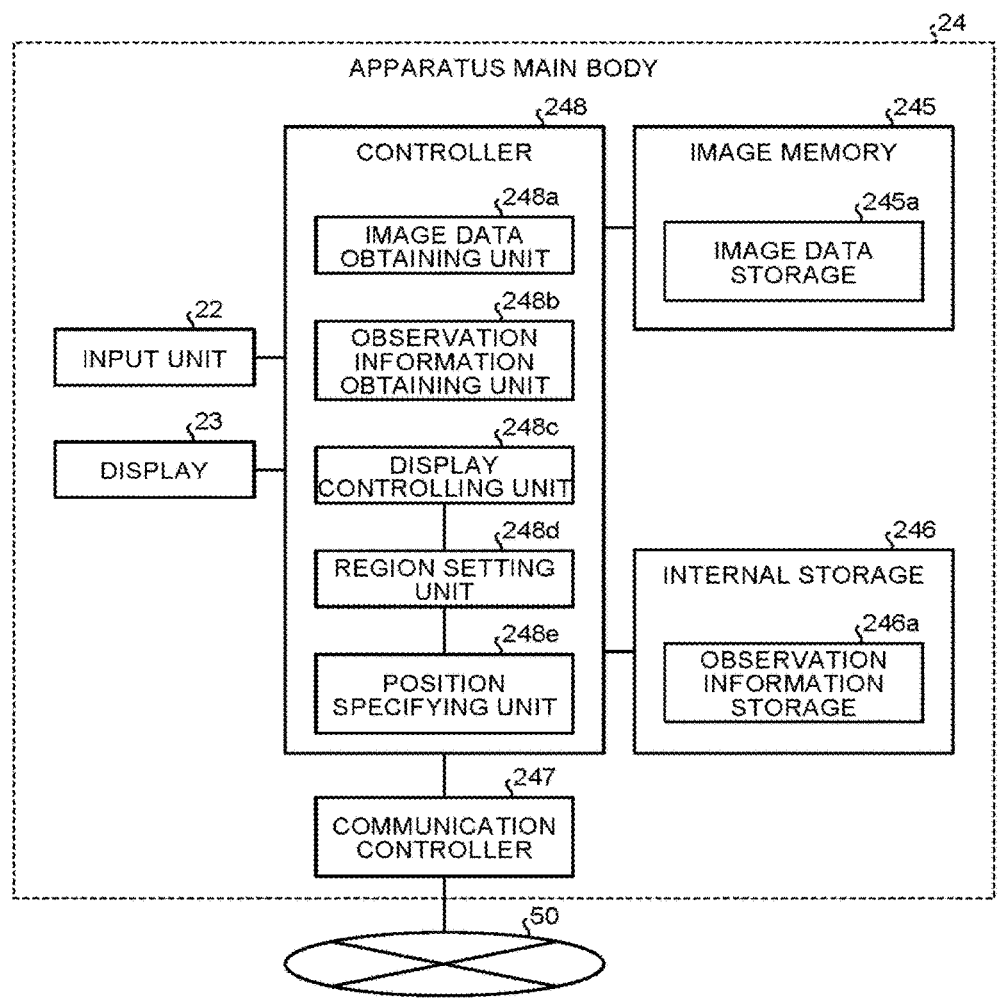
FIG. 23 is a diagram of a detailed exemplary configuration of an ultrasound diagnosis apparatus according to a third embodiment.

FIG. 23 is a diagram of a detailed exemplary configuration of the ultrasound diagnosis apparatus 20 according to the third embodiment. From among the elements included in the ultrasound diagnosis apparatus 20 illustrated in FIG. 4, FIG. 23 illustrates the input unit 22, the display 23, the apparatus main body 24, the image memory 245, the internal storage 246, the communication controller 247, and the controller 248.

As illustrated in FIG. 23, for example, the image memory 245 includes an image data storage 245a. The internal storage 246 includes an observation information storage 246a. Alternatively, the image data storage 245a may be included in the internal storage 246. Similarly, the observation information storage 246a may be included in the image memory 245.

The image data storage 245a is configured to store therein the mammography images of the breast of the patient. An image data obtaining unit 248a (explained later) stores the mammography images into the image data storage 245a.

The observation information storage 246a is configured to store therein observation information related to the mammography images of the patient. An observation information obtaining unit 248b (explained later) stores the observation information into the observation information storage 246a.

Further, as illustrated in FIG. 23, for example, the controller 248 includes the image data obtaining unit 248a, the observation information obtaining unit 248b, a display controlling unit 248c, a region setting unit 248d, and a position specifying unit 248e.

The image data obtaining unit 248a is configured to obtain the mammography images of the breast of the patient. In this situation, the image data obtaining unit 248a obtains a mammography image in an MLO direction and a mammography image in a CC direction for each of the left and the right breasts of the patient.

More specifically, the image data obtaining unit 248a obtains the mammography images related to the patient serving as a diagnosis target, by communicating with the image processing apparatus 30 via the communication controller 247 and stores the obtained mammography images into the image data storage 245a. Alternatively, the image data obtaining unit 248a may obtain the mammography images related to the patient serving as the diagnosis target, by communicating with the mammography apparatus 10 via the communication controller 247.

The observation information obtaining unit 248b is configured to obtain the observation information related to the breast of the patient. More specifically, the observation information obtaining unit 248b obtains the observation information of the mammography images related to the patient serving as the diagnosis target, by communicating with the image processing apparatus 30 via the communication controller 247. After that, the observation information obtaining unit 248b stores the obtained observation information into the observation information storage 246a.

The display controlling unit 248c is configured to cause the display 23 to display a reference screen used for referencing the mammography images. More specifically, when having received a display request from the operator via the input unit 22, the display controlling unit 248c causes the display 23 to display the reference screen on which the mammography images and the observation information are arranged, similarly to the display controlling unit 35c described in the first embodiment. In that situation, the display controlling unit 248c uses the mammography images of the patient stored in the image data storage 245a and the observation information of the patient stored in the observation information storage 246a.

The region setting unit 248d is configured to set a region of interest in at least one of the mammography images. More specifically, the region setting unit 248d sets the region of interest in at least one of the mammography images, by using the same method as the one used by the region setting unit 35d described in the first embodiment. For example, the region setting unit 248d sets a region of interest in each of the MLO and the CC images for each of the left and the right breasts of the patient.

The position specifying unit 248e is configured to specify the position information of each of the regions of interest in the schematic drawing that schematically expresses the breast, on the basis of pieces of position information of the regions of interest in the mammography images and the pieces of information indicating the image taking directions. More specifically, the position specifying unit 248e specifies the position information of each of the regions of interest in the schematic drawing, by using the same method as the one used by the position specifying unit 35e described in the first embodiment.

After that, similarly to the position specifying unit 35e described in the first embodiment, the position specifying unit 248e generates display information in which a region indicating the region of interest is arranged in a template of the schematic drawing of the mammary gland region. After that, for example, the position specifying unit 248e causes the display 23 to display the same reference screen as the one illustrated in FIG. 12, on the basis of the generated display information.

As explained above, in the third embodiment, the ultrasound diagnosis apparatus 20 sets the regions of interest in the mammography images of the breast of the patient and specifies and outputs the position information of the region of interest in the schematic drawing that schematically expresses the breast, on the basis of the pieces of position information of the regions of interest in the mammography images and the pieces of information indicating the image taking directions of the mammography images. This arrangement makes it possible, for example, for the ultrasound examination technician to easily understand, by using the ultrasound diagnosis apparatus 20, the position in the schematic drawing corresponding to the regions of interest set in the mammography images. It is therefore possible to improve the level of precision of the mammary gland image diagnosis process.

Fourth Embodiment

In the first to the third embodiments above, the example is explained in which the regions of interest are set on the basis of the operation by the operator; however, possible embodiments are not limited to this example. For instance, another arrangement is acceptable in which a mammary gland parenchyma region is extracted from a mammography image, so that a region of interest in the breast is automatically set on the basis of the extracted mammary gland parenchyma region.

Accordingly, in a fourth embodiment, an example will be explained in which an image display apparatus 140 is configured to extract a mammary gland parenchyma region from a mammography image of the breast of a patient and to specify and display a region of interest in the breast, on the basis of the extracted mammary gland parenchyma region. This arrangement makes it possible for an ultrasound examination technician to perform an ultrasound examination especially carefully on the region in which the density of the mammary gland parenchyma is high within the mammography image. It is therefore possible to improve the level of precision of the mammary gland diagnosis process. In the following sections, the image display apparatus 140 according to the fourth embodiment will be explained in detail.

Figure 24:
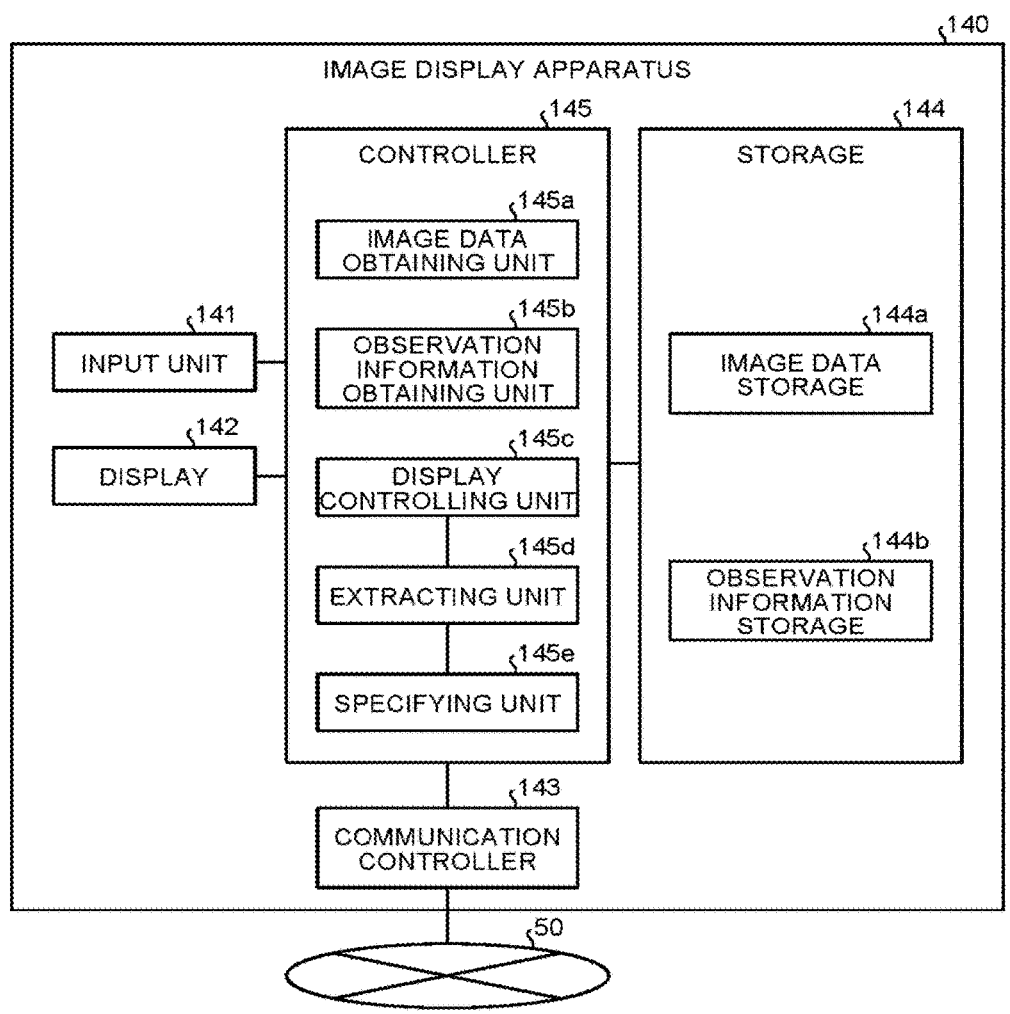
FIG. 24 is a diagram of an exemplary configuration of an image display apparatus according to a fourth embodiment.

FIG. 24 is a diagram of an exemplary configuration of the image display apparatus 140 according to the fourth embodiment. As illustrated in FIG. 24, the image display apparatus 140 includes an input unit 141, a display 142, a communication controller 143, a storage 144, and a controller 145.

The input unit 141 is configured to receive inputs of various types of operations and various types of information from an operator. For example, the input unit 141 may be configured by using a button, a touch panel, and/or a pen tablet.

The display 142 is configured to display a GUI used for receiving the various types of operations from the operator and various types of images. For example, the display 142 may be configured by using a liquid crystal display device or a touch panel.

The communication controller 143 is configured to control communication performed with another apparatus via the network 50. For example, the communication controller 143 may perform wireless communication with the other apparatus by connecting to the network 50 via a wireless LAN.

The storage 144 is a storage device such as a hard disk, a semiconductor memory, or the like and is configured to store various types of information therein. More specifically, the storage 144 includes an image data storage 144a and an observation information storage 144b.

The image data storage 144a is configured to store therein mammography images of the breast of the patient. An image data obtaining unit 145a (explained later) stores the mammography images into the image data storage 144a.

The observation information storage 144b is configured to store therein the observation information related to the mammography images of the patient. An observation information obtaining unit 145b (explained later) stores the observation information into the observation information storage 144b.

The controller 145 includes processing circuitry such as a CPU and a memory and is configured to control operations of the image display apparatus 140 by employing the CPU and the memory to execute various types of computer programs. More specifically, the controller 145 includes the image data obtaining unit 145a, the observation information obtaining unit 145b, a display controlling unit 145c, an extracting unit 145d, and a specifying unit 145e.

The image data obtaining unit 145a is configured to obtain the mammography images of the breast of the patient. In this situation, the image data obtaining unit 145a obtains a mammography image in an MLO direction and a mammography image in a CC direction for each of the left and the right breasts of the patient.

More specifically, the image data obtaining unit 145a obtains the mammography images related to the patient serving as a diagnosis target by communicating with the image processing apparatus 30 via the communication controller 143 and stores the obtained mammography images into the image data storage 144a. Alternatively, the image data obtaining unit 145a may obtain the mammography images related to the patient serving as the diagnosis target, by communicating with the mammography apparatus 10 via the communication controller 143.

The observation information obtaining unit 145b is configured to obtain the observation information related to the breast of the patient. More specifically, the observation information obtaining unit 145b obtains the observation information of the mammography images related to the patient serving as the diagnosis target by communicating with the image processing apparatus 30 via the communication controller 143. Further, the observation information obtaining unit 145b stores the obtained observation information into the observation information storage 144b.

The display controlling unit 145c is configured to cause the display 142 to display a reference screen used for referencing the mammography images. More specifically, when having received a display request from the operator via the input unit 141, the display controlling unit 145c reads the mammography images related to the patient serving as the diagnosis target from the image data storage 144a and reads the observation information related to the patient serving as the diagnosis target from the observation information storage 144b. Further, the display controlling unit 145c causes the display 142 to display the reference screen on which the mammography images and the observation information that were read are arranged.

Figure 25:
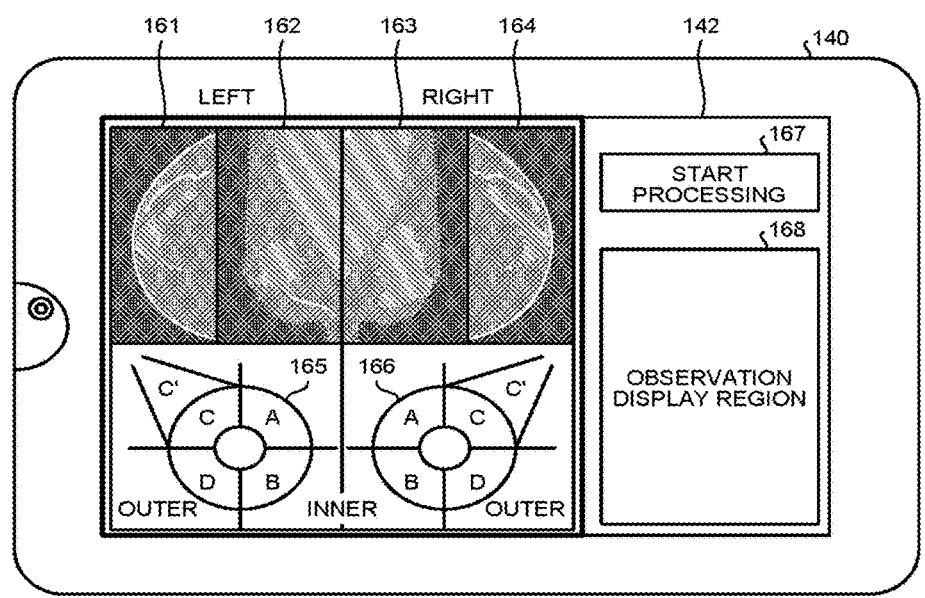
FIG. 25 is a drawing of an example of a reference screen displayed by a display controlling unit according to the fourth embodiment.

FIG. 25 is a drawing of an example of the reference screen displayed by the display controlling unit 145c according to the fourth embodiment. For example, as illustrated in FIG. 25, the display controlling unit 145c causes the display 142 to display a reference screen on which mammography images 161 to 164, mammary gland region schematic drawings 165 and 166, a processing start button 167, and an observation display region 168 are arranged.

In this situation, the mammography image 161 is a mammography image in a CC direction related to the left breast of the patient. The mammography image 162 is a mammography image in an MLO direction related to the left breast of the patient. The mammography image 163 is a mammography image in an MLO direction related to the right breast of the patient. The mammography image 164 is a mammography image in a CC direction related to the right breast of the patient. Further, the schematic drawing 165 indicates a mammary gland region of the left breast of the patient. The schematic drawing 166 indicates a mammary gland region of the right breast of the patient. The processing start button 167 is a button used for receiving an instruction to start a mammary gland parenchyma region extracting process, from the operator. The observation display region 168 is a region used for displaying the observation information related to the mammography images of the patient.

Returning to the description of FIG. 24, the extracting unit 145d is configured to extract mammary gland parenchyma regions from the mammography images of the breast of the patient. Further, the extracting unit 145d is configured to display the extracted mammary gland parenchyma regions so as to be superimposed on the mammography images displayed on the reference screen by the display controlling unit 145c. In this situation, the extracting unit 145d extracts a mammary gland parenchyma region from each of the MLO-direction and CC-direction mammography images for each of the left and the right breasts of the patient.

More specifically, when the operator of the image display apparatus 140 has pressed the processing start button 167 on the reference screen, the extracting unit 145d reads the mammography images related to the patient serving as the diagnosis target from the image data storage 144a and extracts the mammary gland parenchyma regions from the read mammography images. In this situation, the extracting unit 145d may extract, in advance, the mammary gland parenchyma regions from the mammography images at the point in time when the image data obtaining unit 145a has obtained the mammography images of the patient.

For example, the extracting unit 145d extracts the mammary gland parenchyma regions by performing a threshold process on the basis of a distribution of brightness values in the mammography image.

Figure 26:
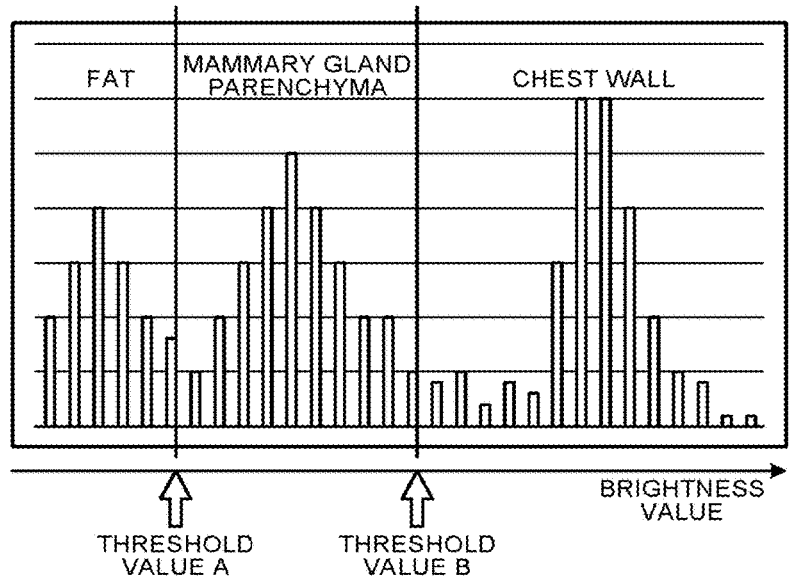
FIG. 26 is a first drawing for explaining a process of extracting a mammary gland parenchyma region performed by an extracting unit according to the fourth embodiment.
Figure 27:
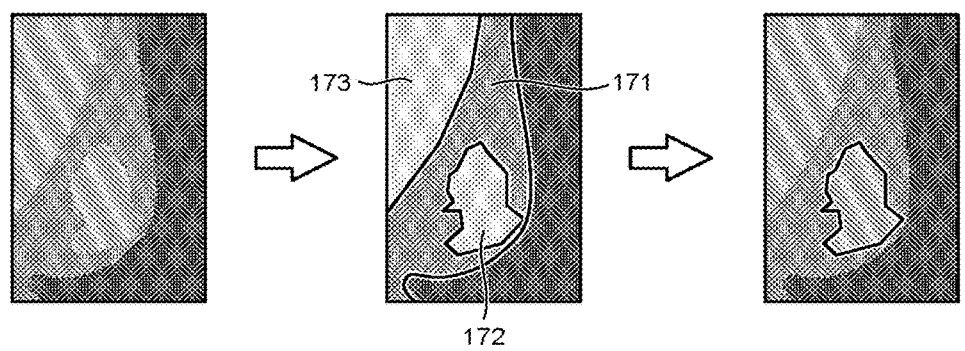
FIG. 27 is a second drawing for explaining the process of extracting the mammary gland parenchyma region performed by the extracting unit according to the fourth embodiment.

FIGS. 26 and 27 are drawings for explaining a process of extracting a mammary gland parenchyma region performed by the extracting unit 145d according to the fourth embodiment. Generally speaking, it is known that mammary gland parenchyma and the pectoralis major muscle are rendered in white, whereas fat is rendered in black in mammography images, because mammary gland parenchyma, the pectoralis major muscle, and fat have mutually-different X-ray transmission coefficients. For this reason, by analyzing the characteristics of a distribution of brightness values in a mammography image by using a histogram of the brightness values, it is possible to extract a region that is presumed to be mammary gland parenchyma.

For example, as illustrated in FIG. 26, the extracting unit 145d divides the brightness values of the pixels included in the mammography image into three ranges, by using a threshold value A for separating brightness values of fat from brightness values of mammary gland parenchyma and a threshold value B for separating brightness values of mammary gland parenchyma and brightness values of the chest wall. In this manner, the extracting unit 145d extracts a region in which the density of mammary gland parenchyma is high as the mammary gland parenchyma region, by using the threshold value A indicating a lower limit and the threshold value B indicating an upper limit with respect to the brightness values corresponding to the mammary gland parenchyma.

Further, for example, the extracting unit 145d assigns a pixel value "0" to each of the pixels of which the brightness values are equal to or smaller than the threshold value A, assigns a pixel value "1" to each of the pixels of which the brightness values are larger than the threshold value A but are equal to or smaller than the threshold value B, and assigns a pixel value "2" to each of the pixels of which the brightness values are larger than the threshold value B. As a result, as illustrated in the left and the middle sections of FIG. 27, the mammography image serving as a processing target is three-valued and is separated into a region 171 corresponding to the pixel value "0", a region 172 corresponding to the pixel value "1", and a region 173 corresponding to the pixel value "2". In this situation, the region 171 is a region representing the fat, whereas the region 172 is a region representing the mammary gland parenchyma, and the region 173 is a region representing the chest wall. After that, the extracting unit 145d extracts the mammary gland parenchyma region, by extracting the region 172 corresponding to the pixel value "1". In this situation, the extracting unit 145d may extract the outline (the boundary) of the region corresponding to the pixel value "1", as the mammary gland parenchyma region. After that, as illustrated in the right section of FIG. 27, the extracting unit 145d displays the extracted mammary gland parenchyma region so as to be superimposed on the mammography image displayed on the reference screen by the display controlling unit 145c.

Alternatively, the extracting unit 145d may extract the mammary gland parenchyma region by using any other edge detecting method. For example, the extracting unit 145d may extract the mammary gland parenchyma region by using a derivative edge detecting method, on the basis of the distribution of the brightness values in the mammography image. The derivative edge detecting method is a method by which the zero crossing of a second derivative in the gradient direction of a gradient in brightness values is detected with respect to a change in the brightness values. By using this method, it is possible to calculate the position of an edge with an accuracy of subpixels.

Alternatively, the extracting unit 145d may extract the mammary gland parenchyma region by using a Sobel operator on the basis of the distribution of the brightness values in the mammography image. The Sobel operator is used in a method for calculating the intensity (the derivative) of a gradient in brightness values by performing a local multiply-accumulation operation with respect to a change in the brightness values. For example, the Sobel operator uses coefficient matrices $f_x$ and $f_y$ presented in Expression (4) below, where $f_x$ is a coefficient matrix for detecting an edge in the column direction, whereas $f_y$ is a coefficient matrix for detecting an edge in the row direction.

$$f_x : \begin{pmatrix} -1 & 0 & 1 \\ -2 & 0 & 2 \\ -1 & 0 & 1 \end{pmatrix} \qquad f_y : \begin{pmatrix} -1 & -2 & -1 \\ 0 & 0 & 0 \\ 1 & 2 & 1 \end{pmatrix} \qquad (4)$$

Further, with the use of Expression (5) presented below, the intensity $|\Delta f|$ of the gradient in the brightness values is calculated.

$$|\Delta f| = \sqrt{f_x^2 + f_y^2} \qquad (5)$$

Furthermore, with the use of Expression (6) presented below, the direction θ of the edge is calculated.

$$\theta = \tan^{-1}(f_x/f_y) \qquad (6)$$

Returning to the description of FIG. 24, the specifying unit 145e is configured to specify a region of interest in the breast of the patient, on the basis of the mammary gland parenchyma regions extracted by the extracting unit 145d. Further, the specifying unit 145e is configured to display the specified region of interest in a schematic drawing of the mammary gland region displayed on the reference screen by the display controlling unit 145c. In this situation, the specifying unit 145e specifies the region of interest in the breast, on the basis of the mammary gland parenchyma region extracted by the extracting unit 145d from each of the MLO-direction and CC-direction mammography images, for each of the left and the right breasts of the patient.

For example, the specifying unit 145e specifies an overlapping section between the region set by the operator on the basis of the mammary gland parenchyma region extracted from the MLO-direction mammography image and the region set by the operator on the basis of the mammary gland parenchyma region extracted from the CC-direction mammography image, as the region of interest. By specifying the overlapping section between the regions set in the mammography images in the mutually-different directions as the region of interest in this manner, it is possible to more accurately indicate the region on which the ultrasound examination technician should perform an ultrasound examination especially carefully.

Figure 28:
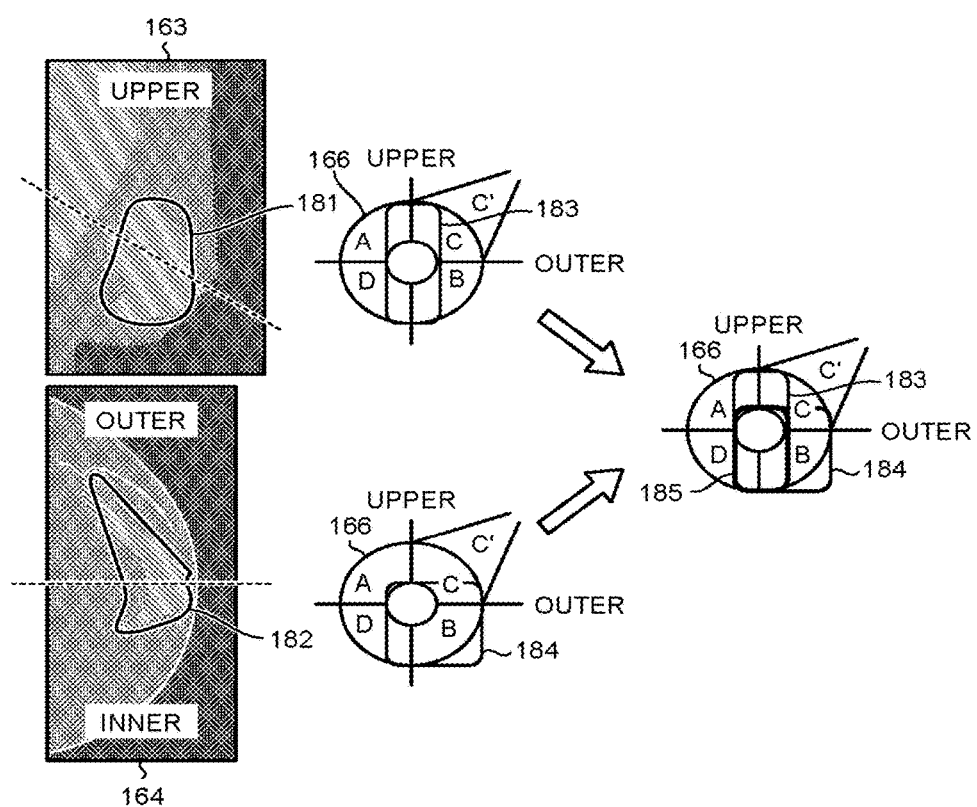
FIG. 28 is a drawing for explaining a process of specifying a region of interest performed by a specifying unit according to the fourth embodiment.

FIG. 28 is a drawing for explaining a process of specifying the region of interest performed by the specifying unit 145e according to the fourth embodiment. Although an example will be explained below in which a region of interest in the right breast of the patient is specified, it is also possible to specify a region of interest in the left breast by using the same method.

As illustrated in the top left section of FIG. 28, on the reference screen, a mammary gland parenchyma region 181 extracted by the extracting unit 145d from an MLO-direction mammography image 163 is displayed in the MLO-direction mammography image. Further, as illustrated in the bottom left section of FIG. 28, on the reference screen, a mammary gland parenchyma region 182 extracted by the extracting unit 145d from a CC-direction mammography image 164 is displayed in the CC-direction mammography image.

When the mammary gland parenchyma regions are displayed by the extracting unit 145d, the specifying unit 145e receives, from the operator, an operation to set a region in a schematic drawing 166 of the mammary gland region via the input unit 141. More specifically, as illustrated in the top middle section of FIG. 28, the specifying unit 145e receives the operation performed by the operator to set a region 183 in the schematic drawing 166 of the mammary gland region, on the basis of the mammary gland parenchyma region 181 displayed in the MLO-direction mammography image 163. Further, as illustrated in the bottom middle section of FIG. 28, the specifying unit 145e receives the operation performed by the operator to set a region 184 in the schematic drawing 166 of the mammary gland region, on the basis of the mammary gland parenchyma region 182 displayed in the CC-direction mammography image 164. After that, when the two regions 183 and 184 have been set by the operator, the specifying unit 145e specifies the overlapping section of the regions, as a region of interest 185, as illustrated in the right section of FIG. 28.

In this situation, for example, the specifying unit 145e may automatically set a region of interest, instead of receiving the setting of a region of interest from the operator. For example, the specifying unit 145e may specify the region of interest by setting the length of the region of interest in one direction on the basis of the size of the mammary gland parenchyma region extracted from the MLO-direction mammography image and setting the length of the region of interest in the other direction on the basis of the size of the mammary gland parenchyma region extracted from the CC-direction mammography image.

Figure 29:
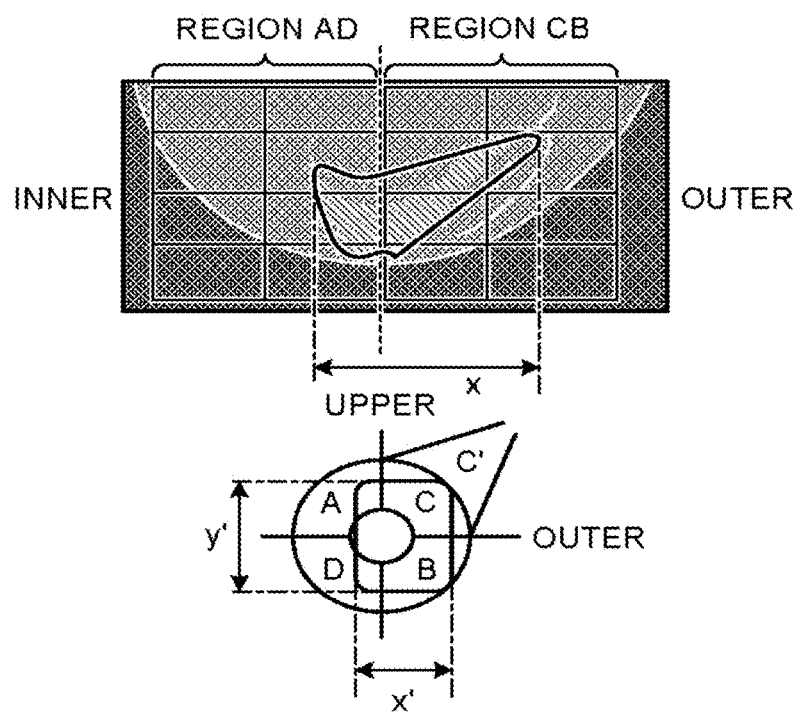
FIG. 29 is a drawing for explaining another example of a process of specifying a region of interest performed by the specifying unit according to the fourth embodiment.

FIG. 29 is a drawing for explaining the other example of the process of specifying a region of interest performed by the specifying unit 145e according to the fourth embodiment. For example, as illustrated in the upper section of FIG. 29, the specifying unit 145e sets correspondence relationships between the positions of the regions in the mammography image and the positions of the regions in the schematic drawing of the mammary gland region, in advance. Further, as illustrated in the lower section of FIG. 29, the specifying unit 145e calculates the length x of the mammary gland parenchyma region in the inner-outer direction in the CC-direction mammography image and sets the length x' of the region of interest in the inner-outer direction, in accordance with the calculated length x. In this situation, the specifying unit 145e sets the length y' of the region of interest in the upper-lower direction, in accordance with the length of the mammary gland parenchyma region in the upper-lower direction in the MLO-direction mammography image.

Figure 30:
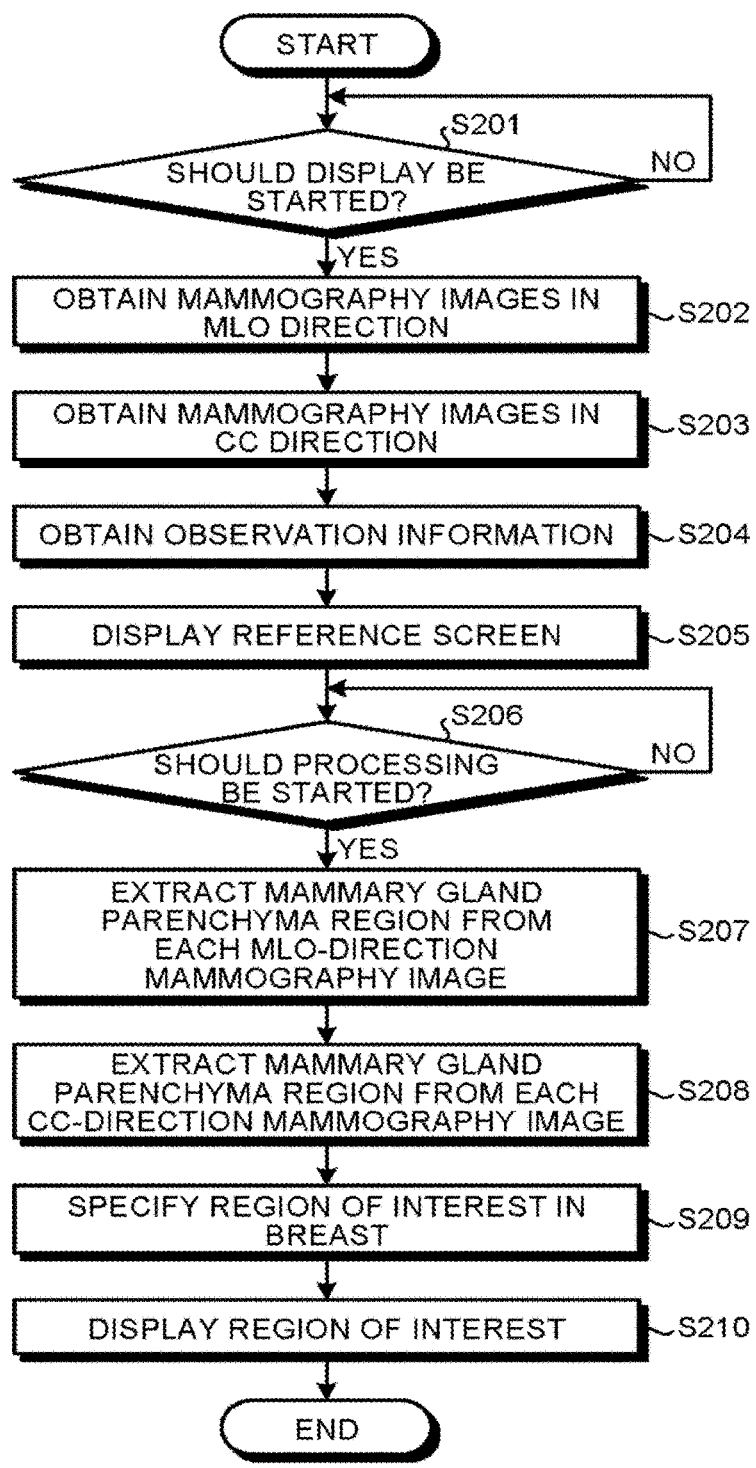
FIG. 30 is a flowchart of a processing procedure of a process performed by an image display apparatus according to the fourth embodiment.

FIG. 30 is a flowchart of a processing procedure of a process performed by the image display apparatus 140 according to the fourth embodiment. As illustrate in FIG. 30, when the image display apparatus 140 has received an instruction to display mammography images and observation information from the operator (step S201: Yes), the image data obtaining unit 145a obtains a mammography image in an MLO direction and a mammography image in a CC direction for each of the left and the right breasts of the patient (steps S202 and S203). Further, the observation information obtaining unit 145b obtains observation information related to the breast of the patient (step S204).

Subsequently, the display controlling unit 145c causes the display 142 to display a reference screen used for referencing the mammography images (step S205). After that, when the operator has pressed the processing start button 167 on the reference screen (step S206: Yes), the extracting unit 145d extracts a mammary gland parenchyma region from each of the MLO-direction and CC-direction mammography images of the patient (steps S207 and S208).

Subsequently, on the basis of the mammary gland parenchyma region extracted by the extracting unit 145d from each of the MLO-direction and CC-direction mammography images, the specifying unit 145e specifies a region of interest in the breast (step S209). Further, the specifying unit 145e causes the specified region of interest to be displayed on the reference screen displayed by the display controlling unit 145c (step S210).

As explained above, in the fourth embodiment, the image display apparatus 140 extracts the mammary gland parenchyma regions from the mammography images of the breast of the patient and specifies and displays the region of interest in the breast, on the basis of the extracted mammary gland parenchyma regions. This arrangement makes it possible for the ultrasound examination technician to perform an ultrasound examination especially carefully on the region in which the density of the mammary gland parenchyma is high within the mammography image. It is therefore possible to improve the level of precision of the mammary gland image diagnosis process.

Fifth Embodiment

In the fourth embodiment above, the example is explained in which the image display apparatus 140 specifies the region of interest by extracting the mammary gland parenchyma regions from the mammography images of the patient and displays the specified region of interest. In contrast, in a fifth embodiment, an example will be explained in which the image processing apparatus 130 specifies a region of interest by extracting mammary gland parenchyma regions from mammography images of a patient, whereas the image display apparatus 40 displays the region of interest specified by the image processing apparatus 130. The configurations of the apparatuses included in a medical information processing system according to the fifth embodiment are the same as those illustrated in FIG. 1.

Figure 31:
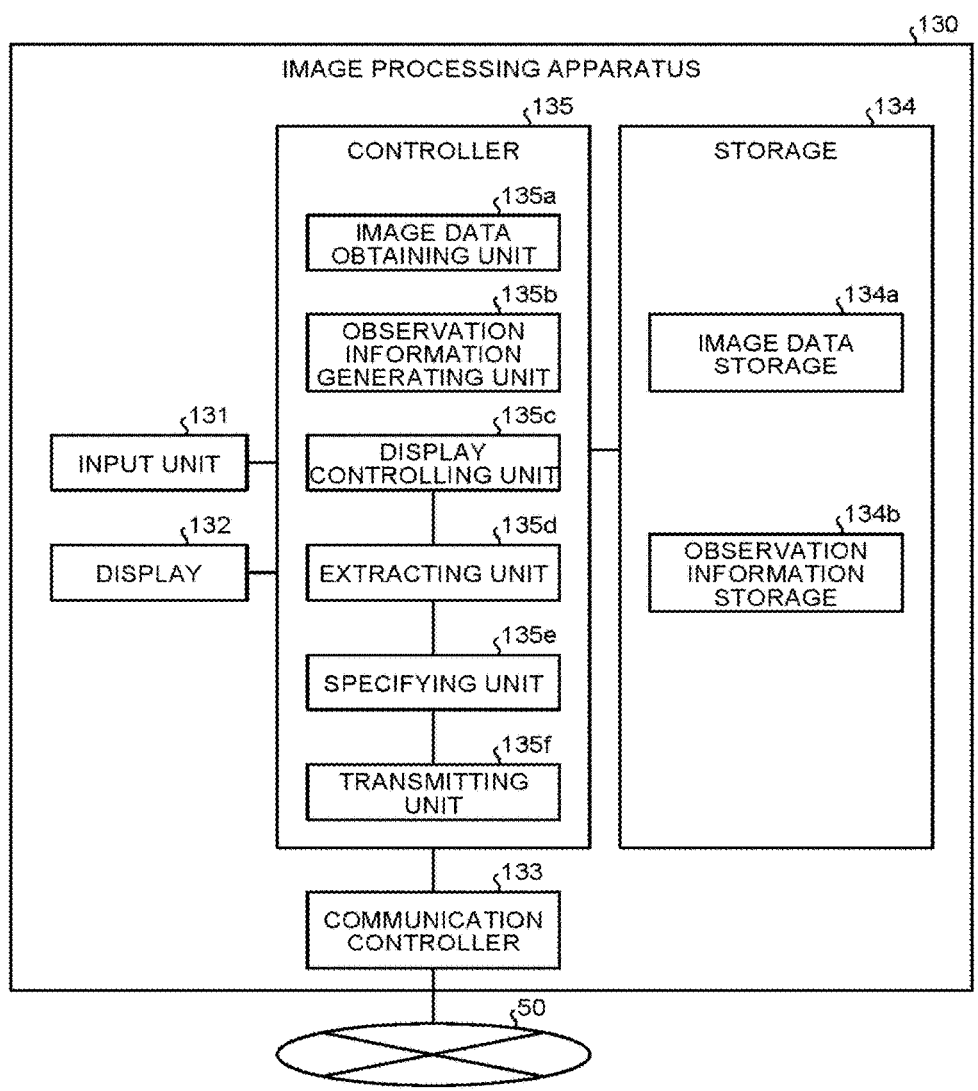
FIG. 31 is a diagram of an exemplary configuration of an image processing apparatus according to a fifth embodiment.

FIG. 31 is a diagram of an exemplary configuration of the image processing apparatus 130 according to the fifth embodiment. As illustrated in FIG. 31, the image processing apparatus 130 includes an input unit 131, a display 132, a communication controller 133, a storage 134, and a controller 135.

The input unit 131 is configured to receive inputs of various types of operations and various types of information from the operator. For example, the input unit 131 may be configured by using a keyboard, a mouse, a button, a trackball, and/or a touch panel.

The display 132 is configured to display a GUI used for receiving the various types of operations from the operator and various types of images. For example, the display 132 may be configured by using a liquid crystal display device, a Cathode Ray Tube (CRT) display device, or a touch panel.

The communication controller 133 is configured to control communication performed with another apparatus via the network 50. For example, the communication controller 133 may be configured by using a network card or a network adaptor and may perform the communication with the other apparatus by connecting to the network 50 via an Ethernet (registered trademark) LAN. Further, for example, the communication controller 133 may perform wireless communication with the other apparatus by connecting to the network 50 via a wireless LAN.

The storage 134 is a storage device such as a hard disk, a semiconductor memory, or the like and is configured to store various types of information therein. More specifically, the storage 134 includes an image data storage 134a and an observation information storage 134b.

The image data storage 134a is configured to store therein mammography images of the breast of the patient. An image data obtaining unit 135a (explained later) stores the mammography images into the image data storage 134a.

The observation information storage 134b is configured to store therein the observation information related to the mammography images of the patient. An observation information generating unit 135b (explained later) stores the observation information into the observation information storage 134b.

The controller 135 includes processing circuitry such as a CPU and a memory and is configured to control operations of the image processing apparatus 130 by employing the CPU and the memory to execute various types of computer programs. More specifically, the controller 135 includes the image data obtaining unit 135a, the observation information generating unit 135b, a display controlling unit 135c, an extracting unit 135d, a specifying unit 135e, and a transmitting unit 135f.

The image data obtaining unit 135a is configured to obtain the mammography images of the breast of the patient. In this situation, the image data obtaining unit 135a obtains a mammography image in an MLO direction and a mammography image in a CC direction for each of the left and the right breasts of the patient. More specifically, the image data obtaining unit 135a obtains the mammography images related to the patient serving as a diagnosis target by communicating with the mammography apparatus 10 via the communication controller 133.

The observation information generating unit 135b is configured to generate the observation information related to the mammography images of the patient, on the basis of an observation input by the operator. More specifically, the observation information generating unit 135b receives an input of the observation related to the mammography images from a mammography examination technician via the input unit 131. Further, the observation information generating unit 135b generates the observation information indicating the received observation and stores the generated observation information into the observation information storage 134b.

The display controlling unit 135c is configured to cause the display 132 to display a reference screen used for referencing the mammography images. More specifically, when having received a display request from the operator via the input unit 131, the display controlling unit 135c causes the display 132 to display the reference screen on which the mammography images and the observation information are arranged, similarly to the display controlling unit 145c described in the fourth embodiment. In that situation, the display controlling unit 135c uses the mammography images of the patient stored in the image data storage 134a and the observation information of the patient stored in the observation information storage 134b.

The extracting unit 135d is configured to extract mammary gland parenchyma regions from the mammography images of the breast of the patient. Further, the extracting unit 135d is configured to display the extracted mammary gland parenchyma regions so as to be superimposed on the mammography images displayed on the reference screen by the display controlling unit 135c. In this situation, the extracting unit 135d extracts a mammary gland parenchyma region from each of the MLO-direction and CC-direction mammography images for each of the left and the right breasts of the patient.

More specifically, when the operator of the image processing apparatus 130 has pressed the processing start button on the reference screen, the extracting unit 135d reads the mammography images related to the patient serving as the diagnosis target from the image data storage 134a and extracts the mammary gland parenchyma regions from the read mammography images, by using the same method as the one used by the extracting unit 145d described in the fourth embodiment. In this situation, the extracting unit 135d may extract, in advance, the mammary gland parenchyma regions from the mammography images at the point in time when the image data obtaining unit 135a has obtained the mammography images of the patient.

The specifying unit 135e is configured to specify a region of interest in the breast of the patient, on the basis of the mammary gland parenchyma regions extracted by the extracting unit 135d. Further, the specifying unit 135e is configured to display the specified region of interest in a schematic drawing of the mammary gland region displayed on the reference screen by the display controlling unit 135c. In this situation, the specifying unit 135e specifies the region of interest in the breast, on the basis of the mammary gland parenchyma region extracted by the extracting unit 135d from each of the MLO-direction and CC-direction mammography images, for each of the left and the right breasts of the patient.

More specifically, by using the same method as the one used by the specifying unit 145e described in the fourth embodiment, the specifying unit 135e specifies the region of interest in the breast of the patient on the basis of the mammary gland parenchyma regions extracted by the extracting unit 135d and displays the specified region of interest on the reference screen.

In response to an instruction from the operator, the transmitting unit 135f is configured to transmit information indicating the region of interest specified by the specifying unit 135e, to the image display apparatus 40. More specifically, the transmitting unit 135f receives an instruction to transmit the display information, from the operator of the image processing apparatus 130 via the input unit 131. When having received the instruction to transmit the display information, the transmitting unit 135f generates the display information for displaying a screen including the same information as that on the reference screen after the region of interest has been specified by the specifying unit 135e and transmits the generated display information to the image display apparatus 40. For example, the transmitting unit 135f generates the display information for displaying, on the reference screen displayed by the display controlling unit 135c, a screen on which the mammary gland parenchyma regions extracted by the extracting unit 135d are superimposed on the mammography images and on which the region of interest specified by the specifying unit 135e is indicated in the schematic drawing of the mammary gland region, and transmits the generated display information to the image display apparatus 40.

In this situation, for example, in response to a request from the image display apparatus 40, the transmitting unit 135f may transmit information indicating the region of interest specified by the specifying unit 135e to the image display apparatus 40. In that situation, for example, the transmitting unit 135f receives a request for the display information from the image display apparatus 40 via the communication controller 133. Further, when having received the request for the display information, the transmitting unit 135f generates the display information described above and transmits the display information to the image display apparatus 40 that transmitted the request.

As explained above, in the fifth embodiment, the image processing apparatus 130 extracts the mammary gland parenchyma regions from the mammography images of the breast of the patient and specifies the region of interest in the breast on the basis of the extracted mammary gland parenchyma regions. Further, the image display apparatus 40 displays the information indicating the region of interest specified by the image processing apparatus 130. For example, this arrangement makes it possible for the mammography examination technician to specify the region of interest by using the image processing apparatus 130 and for the ultrasound examination technician to perform an ultrasound examination while using the image display apparatus 40, especially carefully on the region of interest specified by the mammography examination technician. As a result of the mammography examination technician specifying the region of interest in this manner, it is possible to further improve the level of precision of the mammary gland image diagnosis.

In the fifth embodiment, the example is explained in which the extracting unit 135d extracts the mammary gland parenchyma regions from the mammography images, when the operator of the image processing apparatus 130 has pressed the processing start button on the reference screen. However, for example, another arrangement is acceptable in which the extracting unit 135d extracts the mammary gland parenchyma regions from the mammography images, when having received a request to start the processing from the image display apparatus 40. In that situation, for example, in response to a request from the image display apparatus 40, the display controlling unit 135c transmits, in advance, the information for displaying the reference screen on which the mammography images and the observation information are arranged, to the image display apparatus 40. Further, when the operator of the image display apparatus 40 has instructed to start the processing via the reference screen, the extracting unit 135d receives the request to start the processing from the image display apparatus 40 via the network 50.

Sixth Embodiment

In the first and the fifth embodiments above, the example is explained in which the image display apparatus 40 displays the region of interest in the breast of the patient. In contrast, in a sixth embodiment, an example will be explained in which the ultrasound diagnosis apparatus 20 extracts mammary gland parenchyma regions from the mammography images of the patient, specifies a region of interest, and displays the specified region of interest. The configurations of the apparatuses included in a medical information processing system according to the sixth embodiment are the same as those illustrated in FIG. 1.

Figure 32:
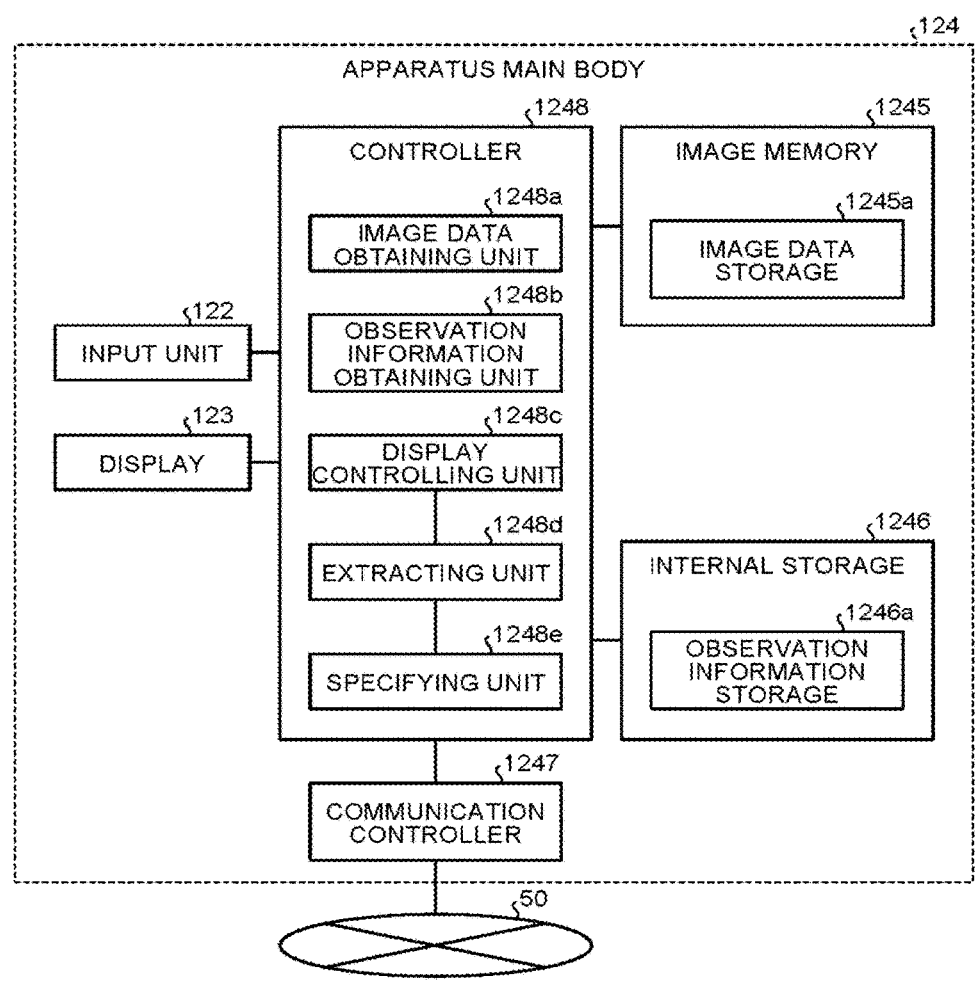
FIG. 32 is a diagram of a detailed exemplary configuration of an ultrasound diagnosis apparatus according to a sixth embodiment.

FIG. 32 is a diagram of a detailed exemplary configuration of the ultrasound diagnosis apparatus 20 according to the sixth embodiment. From among the elements included in the ultrasound diagnosis apparatus 20 illustrated in FIG. 4, FIG. 32 illustrates an input unit 122, a display 123, an apparatus main body 124, an image memory 1245, an internal storage 1246, a communication controller 1247, and a controller 1248.

As illustrated in FIG. 32, for example, the image memory 1245 includes an image data storage 1245a, whereas the internal storage 1246 includes an observation information storage 1246a. Alternatively, the image data storage 1245a may be included in the internal storage 1246. Similarly, the observation information storage 1246a may be included in the image memory 1245.

The image data storage 1245a is configured to store therein the mammography images of the breast of the patient. An image data obtaining unit 1248a (explained later) stores the mammography images into the image data storage 1245a.

The observation information storage 1246a is configured to store therein observation information related to the mammography images of the patient. An observation information obtaining unit 1248b (explained later) stores the observation information into the observation information storage 1246a.

Further, as illustrated in FIG. 32, for example, the controller 1248 includes the image data obtaining unit 1248a, the observation information obtaining unit 1248b, a display controlling unit 1248c, an extracting unit 1248d, and a specifying unit 1248e.

The image data obtaining unit 1248a is configured to obtain the mammography images of the breast of the patient. In this situation, the image data obtaining unit 1248a obtains a mammography image in an MLO direction and a mammography image in a CC direction for each of the left and the right breasts of the patient.

More specifically, the image data obtaining unit 1248a obtains the mammography images related to the patient serving as a diagnosis target, by communicating with the image processing apparatus 30 via the communication controller 1247 and stores the obtained mammography images into the image data storage 1245a. Alternatively, the image data obtaining unit 1248a may obtain the mammography images related to the patient serving as the diagnosis target, by communicating with the mammography apparatus 10 via the communication controller 1247.

The observation information obtaining unit 1248b is configured to obtain the observation information related to the breast of the patient. More specifically, the observation information obtaining unit 1248b obtains the observation information of the mammography images related to the patient serving as the diagnosis target, by communicating with the image processing apparatus 30 via the communication controller 1247. After that, the observation information obtaining unit 1248b stores the obtained observation information into the observation information storage 1246a.

The display controlling unit 1248c is configured to cause the display 123 to display a reference screen used for referencing the mammography images. More specifically, when having received a display request from the operator via the input unit 122, the display controlling unit 1248c causes the display 123 to display the reference screen on which the mammography images and the observation information are arranged, similarly to the display controlling unit 145c described in the fourth embodiment. In that situation, the display controlling unit 1248c uses the mammography images of the patient stored in the image data storage 1245a and the observation information of the patient stored in the observation information storage 1246a.

The extracting unit 1248d is configured to extract mammary gland parenchyma regions from the mammography images of the breast of the patient. Further, the extracting unit 1248d is configured to display the extracted mammary gland parenchyma regions so as to be superimposed on the mammography images displayed on the reference screen by the display controlling unit 1248c. In this situation, the extracting unit 1248d extracts a mammary gland parenchyma region from each of the MLO-direction and CC-direction mammography images for each of the left and the right breasts of the patient.

More specifically, when the operator has pressed the processing start button on the reference screen, the extracting unit 1248d reads the mammography images related to the patient serving as the diagnosis target from the image data storage 1245a and extracts the mammary gland parenchyma regions from the read mammography images, by using the same method as the one used by the extracting unit 145d described in the fourth embodiment. In this situation, the extracting unit 1248d may extract, in advance, the mammary gland parenchyma regions from the mammography images at the point in time when the image data obtaining unit 1248a has obtained the mammography images of the patient.

The specifying unit 1248e is configured to specify a region of interest in the breast of the patient, on the basis of the mammary gland parenchyma regions extracted by the extracting unit 1248d. Further, the specifying unit 1248e is configured to display the specified region of interest in a schematic drawing of the mammary gland region displayed on the reference screen by the display controlling unit 1248c. In this situation, the specifying unit 1248e specifies the region of interest in the breast, on the basis of the mammary gland parenchyma region extracted by the extracting unit 1248d from each of the MLO-direction and CC-direction mammography images, for each of the left and the right breasts of the patient.

More specifically, by using the same method as the one used by the specifying unit 145e described in the fourth embodiment, the specifying unit 1248e specifies the region of interest in the breast of the patient, on the basis of the mammary gland parenchyma regions extracted by the extracting unit 1248d and displays the specified region of interest on the reference screen.

As explained above, in the sixth embodiment, the ultrasound diagnosis apparatus 20 extracts the mammary gland parenchyma regions from the mammography images of the breast of the patient and specifies and displays the region of interest in the breast on the basis of the extracted mammary gland parenchyma regions. With this arrangement, without using the image display apparatus 40, it is possible to indicate, to an ultrasound examination technician, the region on which the examination should be performed especially carefully, via the ultrasound diagnosis apparatus 20.

In the sixth embodiment, the example is explained in which the ultrasound diagnosis apparatus 20 extracts the mammary gland parenchyma regions from the mammography images, specifies the region of interest, and displays the specified region of interest. However, for example, the image processing apparatus 30 may extract the mammary gland parenchyma regions from the mammography images and specify the region of interest, as described in the fifth embodiment.

In that situation, for example, in the ultrasound diagnosis apparatus 20, the communication controller 1247 receives, from the image processing apparatus 30, the mammography images of the breast of the patient and information of the regions of interest in the mammography images via the network 50. Further, the image processor 244 generates ultrasound images on the basis of the data acquired by the ultrasound probe 21. Further, the display controlling unit 1248c causes the display 123 to display the mammography images received by the communication controller 1247, a region of interest, and the ultrasound images generated by the image processor 244.

In the first to the sixth embodiments above, the example is explained in which the mammography images taken by the mammography apparatus 10 are used; however, possible embodiments are not limited to this example. For instance, images taken by a screen film system may be used in place of the mammography images.

Further, in the first to the sixth embodiments above, the example is explained in which the MLO-direction and CC-direction mammography images are used; however, possible embodiments are not limited to this example. For instance, it is acceptable to use mammography images taken in directions other than the MLO and the CC directions.

It is also possible to realize the functions of the controller 35 included in the image processing apparatus 30, the functions of the controller 45 included in the image display apparatus 40, and the functions of the controller 248 included in the ultrasound diagnosis apparatus 20 described in the embodiments above, by using software. For example, the functions of the controlling units may be realized by causing a computer to execute a medical information processing program that defines the procedures of the processes explained as being performed by the controlling units. In that situation, the medical information processing program is, for example, stored in a hard disk, a semiconductor memory device, or the like, so as to be read and executed by processing circuitry such as a processor such as a CPU, an MPU, or the like. Further, the medical information processing program may be distributed as being recorded on a computer-readable recording medium such as a Compact Disk Read-Only Memory (CD-ROM), a Magnetic Optical (MO) disk, or a Digital Versatile Disk (DVD).

According to at least one aspect of the embodiments described above, it is possible to improve the level of precision of the mammary gland image diagnosis process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system comprising:
    a storage configured to store therein a mammography image of a breast of a patient and information indicating an image-taking direction of the mammography image; and
    processing circuitry configured to
        set a region of interest in the mammography image;
        determine a second position of the region of interest according to a distance and a direction from a reference position in a schema that schematically represents a figure of a breast, based on a first position of the region of interest in the mammography image and the information indicating the image-taking direction; and
        display the schema on which the region of interest is displayed at the determined second position.

2. The medical information processing system according to claim 1, wherein
    the storage stores therein a first mammography image of the breast taken in a first image taking direction and a second mammography image of the breast taken in a second image taking direction, and
    the processing circuitry is configured to set a first region of interest in the first mammography image and set a second region of interest in the second mammography image, and
    the processing circuitry is further configured to determine a fifth position of the first region of interest and a sixth position of the second region of interest according to the distance and the direction from the reference position in the schema, based on a third position of the first region of interest in the first mammography image, a fourth position of the second region of interest in the second mammography image, information indicating the first image taking direction, and information indicating the second image taking direction.

3. The medical information processing system according to claim 2, wherein the processing circuitry is further configured to determine a position of an overlapping section between the first region of interest and the second region of interest in the schema, based on the third and fourth position information.

4. The medical information processing system according to claim 1, wherein the processing circuitry is further configured to determine the second position of the region of interest in the schema based on the first position, which is expressed in an apparatus coordinate system of a mammography apparatus that took the mammography image.

5. The medical information processing system according to claim 1, wherein the processing circuitry is further configured to determine the second position of the region of interest in the schema from the mammography image, by performing a predetermined image processing process.

6. The medical information processing system according to claim 1, wherein the processing circuitry is further configured to extract a mammary gland parenchyma region from the mammography image of the breast of the patient and set the region of interest based on the mammary gland parenchyma region.

7. The medical information processing system according to claim 6, wherein the processing circuitry is further configured to extract a first mammary gland parenchyma region from a mammography image of the breast taken in a first image taking direction, extract a second mammary gland parenchyma region from a mammography image of the breast taken in a second image taking direction, and set the region of interest based on the first mammary gland parenchyma region and the second mammary gland parenchyma region.

8. The medical information processing system according to claim 7, wherein the processing circuitry is further configured to set the region of interest by setting a length of the region of interest in one direction based on a size of the first mammary gland parenchyma region and setting a length of the region of interest in another direction based on a size of the second mammary gland parenchyma region.

9. The medical information processing system according to claim 7, wherein the processing circuitry is further configured to set, as the region of interest, an overlapping section between a region set by an operator based on the first mammary gland parenchyma region and a region set by the operator based on the second mammary gland parenchyma region.

10. The medical information processing system according to claim 6, wherein the processing circuitry is further configured to extract the mammary gland parenchyma region by performing a threshold processing process, based on a distribution of brightness values in the mammography image.

11. The medical information processing system according to claim 6, wherein the processing circuitry is further configured to extract the mammary gland parenchyma region by implementing a derivative edge detecting method, based on a distribution of brightness values in the mammography image.

12. The medical information processing system according to claim 6, wherein the processing circuitry is further configured to extract the mammary gland parenchyma region by using a Sobel operator, based on a distribution of brightness values in the mammography image.

13. The medical information processing system according to claim 1, wherein the processing circuitry is further configured to display the schema, as reference information used during an ultrasound diagnosis process.

14. The medical information processing system according to claim 1, wherein the processing circuitry is configured to display the schema corresponding to a patient who is currently undergoing an ultrasound diagnosis process.

15. The medical information processing system according to claim 1, wherein the processing circuitry is further configured to display a position of a blind area in the schema.

16. The medical information processing system according to claim 1, further comprising: an image display apparatus and an image processing apparatus that are connected to each other via a network, wherein
the image display apparatus includes circuitry configured to display the schema, and
the image processing apparatus includes:
the storage; and
the processing circuitry configured to
set the region of interest;
determine the second position of the region of interest; and
transmit information indicating the determined second position to the image display apparatus, in response to an instruction from an operator.

17. The medical information processing system according to claim 1, further comprising: an image display apparatus and an image processing apparatus that are connected to each other via a network, wherein
the image display apparatus includes circuitry configured to display the schema, and
the image processing apparatus includes:
the storage; and
the processing circuitry configured to
set the region of interest;
determine the second position information of the region of interest; and
transmit information indicating the determined second position to the image display apparatus, in response to a request from the image display apparatus.

18. A non-transitory computer readable storage medium having stored therein a computer program causing a computer to execute a process comprising:
setting a region of interest in a mammography image of a breast of a patient;
referring to a storage storing therein the mammography image and information indicating an image taking direction of the mammography image and determining a second position of the region of interest according to a distance and a direction from a reference position in a schema that schematically represents a figure of a breast, based on a first position of the region of interest in the mammography image and the information indicating the image taking direction; and
displaying the schema on which the region of interest is displayed at the determined second position.

19. An ultrasound diagnosis apparatus, comprising:
processing circuitry configured to:
obtain a mammography image of a breast of a patient and information indicating an image taking direction of the mammography image;
set a region of interest in the mammography image;
determine second position information of the region of interest according to a distance and a direction from a reference position in a schema that schematically represents a figure of a breast, based on a first position of the region of interest in the mammography image and the information indicating the image taking direction; and
display the schema on which the region of interest is displayed at the determined second position.

20. An ultrasound diagnosis apparatus, comprising:
a communication controller configured to receive a mammography image of a breast of a patient and information indicating a position of a region of interest set in the mammography image and determined according to a distance and a direction from a reference position in a schema that schematically represents a figure of a breast, from an image processing apparatus via a network;
an ultrasound probe;
an image processor configured to generate an ultrasound image based on data acquired by the ultrasound probe; and
processing circuitry configured to cause a display to display the mammography image, the schema on which the region of interest is displayed at the determined position, and the ultrasound image.

* * * * *